United States Patent
Keren et al.

(10) Patent No.: US 8,876,725 B2
(45) Date of Patent: *Nov. 4, 2014

(54) METHOD AND SYSTEM FOR ESTIMATING EXERCISE CAPACITY

(75) Inventors: Hanan Keren, Kfar-Saba (IL); Daniel Burkhoff, West Harrison, NY (US); Yoav Avidor, Tel-Aviv (IL); Pierre Squara, Enghien-les-Bains (FR)

(73) Assignee: Cheetah Medical, Inc., Wilmington, DE (US)

(*) Notice: Subject to any disclaimer, the term of this patent is extended or adjusted under 35 U.S.C. 154(b) by 894 days.

This patent is subject to a terminal disclaimer.

(21) Appl. No.: 12/527,697

(22) PCT Filed: Feb. 21, 2008

(86) PCT No.: PCT/IL2008/000233
§ 371 (c)(1),
(2), (4) Date: Mar. 24, 2010

(87) PCT Pub. No.: WO2008/102362
PCT Pub. Date: Aug. 28, 2008

(65) Prior Publication Data
US 2010/0191127 A1     Jul. 29, 2010

Related U.S. Application Data

(63) Continuation-in-part of application No. 11/889,395, filed on Aug. 13, 2007.

(60) Provisional application No. 60/902,853, filed on Feb. 23, 2007.

(51) Int. Cl.
*A61B 5/08* (2006.01)
*A61B 5/00* (2006.01)
*A61B 5/02* (2006.01)
*A61B 5/053* (2006.01)
*A61B 5/029* (2006.01)
*A61B 5/0205* (2006.01)

(52) U.S. Cl.
CPC ........... *A61B 5/0535* (2013.01); *A61B 5/0537* (2013.01); *A61B 5/029* (2013.01); *A61B 5/0205* (2013.01); *A61B 5/4869* (2013.01); *A61B 5/02028* (2013.01)
USPC ....................................................... 600/484

(58) Field of Classification Search
USPC .................................. 600/484, 504; 601/41
See application file for complete search history.

(56) References Cited

U.S. PATENT DOCUMENTS

| | | |
|---|---|---|
| 3,340,867 A | 9/1967 | Kubicek et al. |
| 3,851,641 A | 12/1974 | Toole et al. |

(Continued)

FOREIGN PATENT DOCUMENTS

| | | |
|---|---|---|
| WO | WO 82/00581 | 3/1982 |
| WO | WO 96/32883 | 10/1996 |

(Continued)

OTHER PUBLICATIONS

Lele Suhas S et al: "Exercise capacity in hypertrophic cardiomyopathy: Role of stroke volume limitation, heart rate, and diastolic filling characteristics" CIRCULATION, vol. 92, No. 10, 1995, pp. 2886-2894.*

(Continued)

*Primary Examiner* — Michael Kahelin
*Assistant Examiner* — Mitchell E Alter

(57) ABSTRACT

A method of estimating exercise capacity of a subject is disclosed. The method uses output radiofrequency signals transmitted to the subject during exercise and input radiofrequency signals received from the subject during exercise. The method comprises: determining a phase shift of the input radiofrequency signals relative to the output radiofrequency signals; calculating cardiac output based on the phase shift; and using the cardiac output for estimating the exercise capacity of the subject.

21 Claims, 12 Drawing Sheets

(56) References Cited

U.S. PATENT DOCUMENTS

| | | | |
|---|---|---|---|
| 3,871,359 A | 3/1975 | Paccla | |
| 3,874,368 A | 4/1975 | Asrican | |
| 3,914,999 A | 10/1975 | Grandchamp | |
| 4,094,309 A | 6/1978 | Grzenia | |
| 4,153,048 A | 5/1979 | Magrini | |
| RE30,101 E | 9/1979 | Kubicek et al. | |
| 4,437,469 A | 3/1984 | Djordjevich et al. | |
| 4,450,527 A | 5/1984 | Sramek | |
| 4,537,200 A | 8/1985 | Widrow | |
| 4,610,254 A | 9/1986 | Morgan et al. | |
| 4,705,049 A | 11/1987 | John | |
| 4,781,201 A | 11/1988 | Wright et al. | |
| 4,803,431 A | 2/1989 | Sano et al. | |
| 4,805,621 A * | 2/1989 | Heinze et al. | 600/547 |
| 4,852,580 A | 8/1989 | Wood | |
| 4,870,578 A | 9/1989 | Vysin et al. | |
| 4,888,558 A | 12/1989 | Hereikson | |
| 4,926,868 A | 5/1990 | Larsen | |
| 4,953,556 A | 9/1990 | Evans | |
| 5,058,583 A | 10/1991 | Geddes et al. | |
| 5,158,093 A | 10/1992 | Shvartz et al. | |
| 5,178,154 A | 1/1993 | Ackmann et al. | |
| 5,309,917 A | 5/1994 | Wang et al. | |
| 5,316,004 A | 5/1994 | Chesney et al. | |
| 5,423,326 A | 6/1995 | Wang et al. | |
| 5,469,859 A | 11/1995 | Tsoglin et al. | |
| 5,503,157 A | 4/1996 | Sramek | |
| 5,505,209 A | 4/1996 | Reining | |
| 5,529,072 A | 6/1996 | Sramek | |
| 5,615,689 A | 4/1997 | Kotler | |
| 5,642,734 A | 7/1997 | Ruben et al. | |
| 5,685,316 A | 11/1997 | Schookin et al. | |
| 5,817,030 A | 10/1998 | Tarjan et al. | |
| 5,913,826 A | 6/1999 | Blank | |
| 6,015,393 A | 1/2000 | Hovland et al. | |
| 6,053,873 A | 4/2000 | Govari et al. | |
| 6,073,039 A | 6/2000 | Berson | |
| 6,076,015 A | 6/2000 | Hartley et al. | |
| 6,142,941 A | 11/2000 | Benhalima et al. | |
| 6,298,267 B1 | 10/2001 | Rosborough et al. | |
| 6,304,773 B1 | 10/2001 | Taylor et al. | |
| 6,339,722 B1 | 1/2002 | Heethaar et al. | |
| 6,413,223 B1 | 7/2002 | Yang et al. | |
| 6,440,082 B1 | 8/2002 | Joo et al. | |
| 6,485,431 B1 | 11/2002 | Campbell et al. | |
| 6,496,732 B1 | 12/2002 | Wallace | |
| 6,511,438 B2 | 1/2003 | Bernstein et al. | |
| 6,577,897 B1 | 6/2003 | Shurubura et al. | |
| D625,823 S | 10/2010 | Schneider et al. | |
| 8,414,498 B2 | 4/2013 | Keren et al. | |
| 2002/0143368 A1 | 10/2002 | Bakels et al. | |
| 2002/0193689 A1 | 12/2002 | Bernstein et al. | |
| 2003/0083702 A1 | 5/2003 | Stadler et al. | |
| 2003/0109790 A1 | 6/2003 | Stickney et al. | |
| 2003/0120170 A1 | 6/2003 | Zhu et al. | |
| 2003/0158584 A1 | 8/2003 | Cates et al. | |
| 2003/0187341 A1 | 10/2003 | Sackner et al. | |
| 2003/0199779 A1 | 10/2003 | Muhlenberg et al. | |
| 2004/0102908 A1 | 5/2004 | Larson et al. | |
| 2004/0133123 A1 | 7/2004 | Leonhardt et al. | |
| 2005/0004609 A1 | 1/2005 | Stahmann et al. | |
| 2005/0043763 A1 | 2/2005 | Marcovecchio et al. | |
| 2005/0124901 A1 | 6/2005 | Misczynski et al. | |
| 2005/0143634 A1 | 6/2005 | Baker, Jr. et al. | |
| 2005/0192488 A1 | 9/2005 | Bryenton et al. | |
| 2005/0202789 A1 | 9/2005 | Tanabe et al. | |
| 2005/0217674 A1 | 10/2005 | Burton et al. | |
| 2006/0085048 A1 | 4/2006 | Cory et al. | |
| 2006/0122540 A1 | 6/2006 | Zhu et al. | |
| 2006/0200033 A1 | 9/2006 | Keren et al. | |
| 2007/0088221 A1 | 4/2007 | Stahmann | |
| 2007/0191688 A1 | 8/2007 | Lynn | |
| 2008/0154116 A1 | 6/2008 | Duensing et al. | |
| 2008/0255433 A1 | 10/2008 | Prough et al. | |
| 2009/0048497 A1 | 2/2009 | Keren | |
| 2010/0069765 A1 | 3/2010 | Keren | |
| 2011/0218419 A1 | 9/2011 | Keren et al. | |
| 2013/0144177 A1 | 6/2013 | Keren et al. | |

FOREIGN PATENT DOCUMENTS

| | | |
|---|---|---|
| WO | WO 97/11638 | 4/1997 |
| WO | WO 2004/098376 | 11/2004 |
| WO | WO 2004/112606 | 12/2004 |
| WO | WO 2006/087696 | 8/2006 |
| WO | WO 2006087696 A2 * | 8/2006 |
| WO | WO 2007/096054 | 8/2007 |
| WO | WO 2008/102362 | 8/2008 |
| WO | WO 2008/107899 | 9/2008 |
| WO | WO 2008/129535 | 10/2008 |
| WO | WO 2009/022330 | 2/2009 |

OTHER PUBLICATIONS

Raza S B et al: "Filtering Respiration and Lowfrequency Movement Artefacts From the Cardiogenic Electrical Impedance Signal" Medical and Biological Engineering and Computing, Springer, Heildelberg, DE, vol. 30, No. 5, Sep. 1, 1992, pp. 556-561.*
Communication Pursuant to Article 94(3) EPC Dated Feb. 13, 2012 From the European Patent Office Re. Application No. 08719934.5.
Communication Pursuant to Article 94(3) EPC Feb. 12, 2010 From the European Patent Office Re.: Application No. 08738211.5.
Response Dated Apr. 6, 2010 to Official Action of Oct. 6, 2009 From the US Patent and Trademark Office Re.: U.S. Appl. No. 10/556,483.
Examiner's Report Dated Nov. 15, 2010 From the Australian Government, IP Australia Re. Application No. 2006215274.
Response Dated Dec. 29, 2010 to Notice of Reason for Rejection of Sep. 17, 2010 From the Japanese Patent Office Re. Application No. 2006-507622.
Communication Pursuant to Article 94(3) EPC Dated Jan. 26, 2011 From the European Patent Office Re.: Application No. 04731993.4.
Response Dated Jan. 30, 2011 to Communication Pursuant to Article 94(3) EPC of Oct. 20, 2010 From the European Patent Office Re. Application No. 08719934.5.
Invitation Pursuant to Rule 62a(1) EPC Dated Jun. 10, 2010 From the European Patent Office Re. Application No. 06700959.7.
Translation of Official Querry Dated Jul. 1, 2011 From the Japanese Patent Office Re. Application No. 2006-507622.
Response Dated Jul. 25, 2011 to Communication Pursuant to Article 94(3) EPC of Jan. 26, 2011 From the European Patent Office Re.: Application No. 04731993.4.
Response Dated Sep. 11, 2011 to Official Querry Dated Jul. 1, 2011 From the Japanese Patent Office Re. Application No. 2006-507622.
Response Dated Jul. 4, 2010 to Invitation Pursuant to Rule 62a(1) EPC of Jun. 10, 2010 From the European Patent Office Re. Application No. 06700959.7.
Communication Pursuant to Article 94(3) EPC Dated Jul. 8, 2009 From the European Patent Office Re.: Application No. 04731993.4.
Communication Relating to the Results of the Partial International Search Dated Dec. 5, 2008 From the International Searching Authority Re.: Application No. PCT/IL2008/001105.
International Preliminary Report on Patentability Dated Nov. 4, 2009 From the International Preliminary Examining Authority Re.: Application No. PCT/IL2008/001105.
International Preliminary Report on Patentability Dated Aug. 16, 2007 From the International Preliminary Examining Authority Re.: Application No. PCT/IL06/00075.
International Preliminary Report on Patentability Dated Sep. 17, 2009 From the International Bureau of WIPO Re.: Application No. PCT/IL2008/000309.
International Preliminary Report on Patentability Dated Nov. 18, 2008 From the International Preliminary Examining Authority Re.: Application No. PCT/IL04/00395.
International Preliminary Report on Patentability Dated Aug. 26, 2009 From the International Bureau of WIPO Re.: Application No. PCT/IL2008/000233.
International Preliminary Report on Patentability Dated Oct. 29, 2009 From the International Bureau of WIPO Re.: Application No. PCT/IL2008/000509.

(56) References Cited

OTHER PUBLICATIONS

International Search Report Dated Aug. 5, 2008 From the International Searching Authority Re.: Application No. PCT/IL2008/000309.
International Search Report Dated Dec. 6, 2006 From the International Searching Authority Re.: Application No. PCT/IL06/00075.
International Search Report Dated Mar. 22, 2005 From the International Searching Authority Re.: Application No. PCT/IL04/00395.
International Search Report Dated Mar. 27, 2009 From the International Searching Authority Re.: Application No. PCT/IL2008/001105.
International Search Report Dated Jul. 28, 2008 From the International Searching Authority Re.: Application No. PCT/IL2008/000233.
Office Action Dated Dec. 12, 2008 From the State Intellectual Property Office of the People's Republic of China Re.: Application No. 200680012560.2.
Office Action Dated Apr. 24, 2009 From the State Intellectual Property Office of the People's Republic of China Re.: Application No. 200480019436.X.
Office Action Dated Jul. 24, 2009 From the State Intellectual Property Office of the People's Republic of China Re.: Application No. 200680012560.2 and Its Translation Into English.
Official Action Dated Oct. 6, 2009 From the US Patent and Trademark Office Re.: U.S. Appl. No. 10/556,483.
Official Action Dated Feb. 18, 2009 From the US Patent and Trademark Office Re.: U.S. Appl. No. 10/556,483.
Response Dated Nov. 8, 2009 to Communication Pursuant to Article 94(3) EPC of Jul. 8, 2009 From the European Patent Office Re.: Application No. 04731993.4.
Supplementary Partial European Search Report Dated Apr. 9, 2009 From the European Patent Office Re.: Application No. 04731993.4.
Translation of the Official Action Dated Dec. 12, 2008 From the State Intellectual Property Office of the People's Republic of China Re.: Application No. 200680012560.2.
Written Opinion Dated Aug. 5, 2008 From the International Searching Authority Re.: Application No. PCT/IL2008/000309.
Written Opinion Dated Dec. 6, 2006 From the International Searching Authority Re.: Application No. PCT/IL06/00075.
Written Opinion Dated Mar. 22, 2005 From the International Searching Authority Re.: Application No. PCT/I104/00395.
Written Opinion Dated Mar. 27, 2009 From the International Searching Authority Re.: Application No. PCT/IL2008/001105.
Written Opinion Dated Jul. 28, 2008 From the International Searching Authority Re.: Application No. PCT/IL2008/000233.
Bakshi et al. "Circulatory Response in Sleep Apnea Patients During Sleep Before and After CPAP Treatment", Sleep, XO008094214, 28(Suppl.S): A194: 0576, 2005. 19th Annual Meeting of the Associated-Professional-Sleep-Societies, Denver, CO, USA, Jun. 18-23, 2005. Abstract.
Goovaerts et al. "A Wideband High Common Mode Rejection Ratio Amplifier for Multifrequency Impedance Measurement", Medical and Biological Engineering and Computing, XP000784850, 36(6): 761-767, Nov. 1, 1998. Section 2.2 'Lock-in Measurement', p. 761, p. 763, col. 2, Figs.2, 3.
Jellinek et al. "Right Atrial Pressure Predicts Hemodynamic Response to Apneic Positive Airway Pressure", Critical Care Medicine, XP002488470, 28(3): 672-678, Mar. 2000. Database MEDLINE [Online], US National Library of Medicine, Database Accession No. NLM10752813. Abstract.
Kubicek et al. "The Minnesota Impedance Cardiograph—Theory and Applications", Biomedical Engineering, XP001051054, 9(9): 410-416, Sep. 1, 1974. p. 411, Middle col., Figs.1, 2.
Lele et al. "Exercise Capacity in Hypertrophic Cardiomyopathy. Role of Stroke Volume Limitation, Heart Rate, and Diastolic Filling Characteristics", Circulation, XP002487808, 92(10): 2886-2894, 1995.
Lin et al. "Effects of Hypercapnia, Hypoxia, and Rebreathing on Circulatory Response to Apnea", Journal of Applied Physiology Respiratory Environmental and Exercise Physiology, XP008094195, 54(1): 172-177, 1983.

Miyamoto et al. "Cardiorespiratory Dynamics During Sinusoidal and Impulse Exercise in Man", Japanese Journal of Physiology, XP008094022, 33(6): 971-986, 1983.
Myers et al. "Cardiac Output and Cardiopulmonary Responses to Exercise in Heart Failure: Application of a New Bio-Resistance Device", Journal of Cardiac Failure, XP0022287174, 13(8): 629-636, Oct. 6, 2007.
Newman et al. "The Non-Invasive Assessment of Stroke Volume and Cardiac Output by Impedance Cardiography: A Review", Aviation Space and Environmental Medicine, XP008093991, 70(8): 780-789, Aug. 1999.
Raza et al. "Filtering Respiration and Low-Frequency Movement Artefacts From the Cardiogenic Electrical Impedance Signal", Medical and Biological Engineering and Computing, XP000323425, 30(5): 556-561, Sep. 1, 1992. p. 556, r-h col., § 3-p. 557, r-h col., § 1, p. 557, 1-h col., § 3, p. 558, 1-h col., § 2-r-h col., § 1, Fig.3.
Saarelainen et al. "Whole-Body Impedance Recording—A Practical Method for the Diagnosis of Sleep Apnoea", Clinical Physiology and Functional Imaging, XO002488466, 23(2): 110-113, Mar. 2003.
Schumacker et al. "Oxygen Delivery and Uptake Relationships in Patients With Aortic Stenosis", American Journal of Respiratory and Critical Care Medicine, XP002488468, 149(5): 1123-1131, May 1994. Database EMBASE [Online], Database Accession No. EMB-1994152503, 1994. Abstract.
Stoohs et al. "Cardiovascular Changes Associated With Obstructive Sleep Apnea Syndrome", Journal of Applied Physiology, XP002488467, 72(2): 583-589, 1992. Database Biosis [Online], Biosciences Information Service, Database Accession No. PREV199293105800, 1992. Abstract.
Tolle et al. "Reduced Stroke Volume Related to Pleural Pressure in Obstructive Sleep Apnea", Journal of Applied Physiology Respiratory Environmental and Exercise Physiology, XP002488469, 55(6): 1718-1724, 1983. Database BIOSIS [Online], Biosciences Information Service, Database Accession No. PREV198477063246, 1883. Abstract.
Communication Pursuant to Article 94(3) EPC Dated Dec. 29, 2009 From the European Patent Office Re.: Application No. 08710233.1.
Response Dated Sep. 12, 2011 to Official Action of Aug. 31, 2011 From the US Patent and Trademark Office Re. U.S. Appl. No. 11/884,227.
Communication Under Rule 71(3) EPC Dated Oct. 7, 2011 From the European Patent Office Re.: Application No. 08738211.5.
Response Dated Nov. 17, 2011 to Examiner's Report of Nov. 15, 2010 From the Australian Government, IP Australia Re. Application No. 2006215274.
Response Dated Sep. 21, 2010 to Official Action of Jun. 22, 2010 From the US Patent and Trademark Office Re.: U.S. Appl. No. 10/556,483.
Translation of Notice of Reason for Rejection Dated Sep. 17, 2010 From the Japanese Patent Office Re. Application No. 2006-507622.
Response Dated Jul. 21, 2010 to Notice of Reason for Rejection of Apr. 6, 2010 From the Japanese Patent Office Re. Application No. 2006-507622.
Translation of Notice of Reason for Rejection Dated Apr. 6, 2010 From the Japanese Patent Office Re. Application No. 2006-507622.
Official Action Dated Aug. 31, 2011 From the US Patent and Trademark Office Re. U.S. Appl. No. 11/884,227.
Official Action Dated Jun. 22, 2010 From the US Patent and Trademark Office Re.: U.S. Appl. No. 10/556,483.
Response Dated Jun. 28, 2010 to Communication Pursuant to Article 94(3) EPC of Dec. 29, 2009 From the European Patent Office Re.: Application No. 08710233.1.
Communication Pursuant to Article 94(3) EPC Dated Feb. 12, 2010 From the European Patent Office Re.: Application No. 08738211.5.
Response Dated Jun. 3, 2010 to Communication Pursuant to Article 94(3) EPC of Feb. 12, 2010 From the European Patent Office Re.: Application No. 08738211.5.
Communication Pursuant to Article 94(3) EPC Dated Feb. 13, 2012 From the European Patent Office Re. Application No. 08789780.7.
Requisition by the Examiner Dated Jan. 9, 2012 From the Canadian Intellectual Property Office Re. Application No. 2,525,443.
Communication Pursuant to Article 94(3) EPC Dated Pct. 20, 2010 From the European Patent Office Re. Application No. 08719934.5.

(56) References Cited

OTHER PUBLICATIONS

Communication Pursuant to Article 94(3) EPC Dated Feb. 13, 2012 From the European Patent Office Re.: Application No. 08710233.1.
Official Action Dated Nov. 2, 2011 From the US Patent and Trademark Office Re. U.S. Appl. No. 11/884,227.
Delpierre et al. "Doppler Effect With Sound", Electronic Science Tutor, Retrieved From the Internet, 5 P., Oct. 18, 2011.
Ellis "Introduction to Mixers", Retrieved From the Internet, 9 P., 1999.
Notice of Allowance Dated Jan. 30, 2013 From the US Patent and Trademark Office Re.: U.S. Appl. No. 10/556,483.
Official Action Dated Aug. 2, 2012 From the US Patent and Trademark Office Re. U.S. Appl. No. 11/884,227.
Official Action Dated Jul. 24, 2012 From the US Patent and Trademark Office Re. U.S. Appl. No. 12/596,483.
Notice of Allowability Dated Nov. 21, 2012 From the US Patent and Trademark Office Re. U.S. Appl. No. 11/884,227.
Official Action Dated Aug. 9, 2012 From the US Patent and Trademark Office Re. U.S. Appl. No. 11/889,395.
Requisition by the Examiner Dated Jul. 24, 2012 From the Canadian Intellectual Property Office Re. Application No. 2,525,443.
Applicant—Initiated Interview Summary Dated Sep. 17, 2012 From the US Patent and Trademark Office Re. U.S. Appl. No. 11/884,227.
Communication Under Rule 71(3) EPC Dated Oct. 17, 2012 From the European Patent Office Re. Application No. 08789780.7.
Notice of Allowance Dated Oct. 25, 2012 From the US Patent and Trademark Office Re. U.S. Appl. No. 11/884,227.
Official Action Dated Oct. 15, 2012 From the US Patent and Trademark Office Re. U.S. Appl. No. 12/673,037.
Official Action Dated Oct. 23, 2012 From the US Patent and Trademark Office Re. U.S. Appl. No. 12/450,022.
Patent Examination Report Dated Nov. 30, 2012 From the Australian Government, IP Australia Re. Application No. 2008288084.
Patent Examination Report Dated Aug. 1, 2012 From the Australian Government, IP Australia Re. Application No. 2008242145.
Brief Communication for Oral Proceedings on Dec. 10, 2013 Dated Dec. 3, 2013 From the European Patent Office Re. Application No. 04731993.4.
Scofield "A Frequency-Domain Description of a Lock-in-Amplifier", American Journal of Physics, XP009097728, 62(2): 129-133, Feb. 1, 1994.
Official Action Dated Mar. 10, 2014 From the US Patent and Trademark Office Re. U.S. Appl. No. 11/889,395.
Official Action Dated May 2, 2014 From the US Patent and Trademark Office Re. U.S. Appl. No. 13/757,920.
Notice of Allowance Dated May 10, 2013 From the US Patent and Trademark Office Re. U.S. Appl. No. 12/596,483.
Official Action Dated Jun. 17, 2013 From the US Patent and Trademark Office Re. U.S. Appl. No. 12/450,022.
Official Action Dated Apr. 30, 2013 From the US Patent and Trademark Office Re. U.S. Appl. No. 11/889,395.
Restriction Official Action Dated Jul. 3, 2013 From the US Patent and Trademark Office Re. U.S. Appl. No. 13/757,920.
Official Action Dated Aug. 12, 2013 From the US Patent and Trademark Office Re. U.S. Appl. No. 13/757,920.
Summons to Attend Oral Proceedings Pursuant to Rule 115(1) EPC Dated Sep. 5, 2013 From the European Patent Office Re. Application No. 04731993.4.
Requisition by the Examiner Dated Dec. 6, 2013 From the Canadian Intellectual Property Office Re. Application No. 2,597,264.
Supplementary Partial European Search Report Dated Jul. 2, 2014 From the European Patent Office Re. Application No. 06700959.7.

\* cited by examiner

METHOD AND SYSTEM FOR ESTIMATING EXERCISE CAPACITY

RELATED APPLICATIONS

This application is a National Phase of PCT Patent Application No. PCT/IL2008/000233 having International filing date of Feb. 21, 2008, which is a Continuation-In-Part of U.S. patent application Ser. No. 11/889,395, filed on Aug. 13, 2007.

PCT Patent Application No. PCT/IL2008/000233 having International filing date of Feb. 21, 2008, also claims the benefit of U.S. Provisional Patent Application No. 60/902,853, filed on Feb. 23, 2007.

The contents of the above Applications are all incorporated herein by reference.

FIELD AND BACKGROUND OF THE INVENTION

The present invention, in some embodiments thereof, relates to medical application and, more particularly, but not exclusively, to a method and system for estimating exercise capacity.

Congestive Heart Failure (CHF) is a chronic inability of the heart to maintain an adequate output of blood from one or both ventricles of the heart to meet the metabolic demands of the tissues. In patients diagnosed with CHF, sudden cardiac death occurs at 6 to 9 times the rate of the general population.

In CHF subjects having a markedly weakened left ventricle and not markedly weakened right ventricle, blood continues to be pumped into the lungs but is not pumped adequately out of the lungs. As the volume of blood in the lungs increases, the pulmonary vessels enlarge, pulmonary venous congestion develops, and, once the pulmonary capillary pressure rises above a critical point, fluid begins to filter out of the capillaries into the interstitial spaces and alveoli, resulting in pulmonary edema. Pulmonary edema may lead to pleural and abdominal effusion.

In CHF subjects having abnormality in the right heart or the pulmonary arteries, the ability of the heart to move blood forward is limited and congestion occurs behind the right heart. Such congestion causes pleural effusion and/or buildup of fluid in the abdomen.

Numerous techniques for predicting and determining the condition of CHF subjects are known. One such technique is known as exercise capacity test. In exercise capacity test, the respiratory and/or circulatory response of the subject to exercise is analyzed to stratify risk and assess therapy. Analysis of expired gas during exercise is commonly known as cardiopulmonary exercise testing (CPX) or metabolic exercise.

CPX typically includes the calculation or estimation of several measures. Oxygen uptake, also known as $VO_2$, is the rate of oxygen consumption by a patient during an exercise test. Peak $VO_2$ is considered as a measure of a patient's aerobic exercise capacity, and has traditionally been considered a surrogate for maximal cardiac output. Carbon dioxide production rate, also known as $VCO_2$, is the rate of carbon dioxide production by a patient during exercise. $VCO_2$ relative to $VO_2$ is influenced by which substrate is metabolized (fat vs. carbohydrate) and whether anaerobic processes and lactic acid production occur. Known in the art are methods of calculating $VO_2$ and $VCO_2$ by numerical integration of the product of expiratory airflow with $O_2$ and $CO_2$ concentrations.

Attempts have been made to developed techniques for estimating cardiac output during exercise. Generally, direct measurement of cardiac output by thermodilution is considered the "gold standard." Yet, this technique is cumbersome, invasive, and carries an added expense and degree of risk. Several non invasive techniques are described in Leslien et al., "Non-invasive measurement of cardiac output in patients with chronic heart failure,", Blood Press Monit 2004, 9:277-280; Engoren et al., "Comparison of cardiac output determined by bioimpedance, thermodilution, and the Fick method,", Am J Crit. Care 2005, 14:40-45; and Newman et al., "The non-invasive assessment of stroke volume and cardiac output by impedance cardiography: a review," Aviat Space Environ Med, 1999, 70:780-789.

SUMMARY OF THE INVENTION

According an aspect of the present invention there is provided a method of estimating exercise capacity of a subject using output radiofrequency signals transmitted to the subject during exercise and input radiofrequency signals received from the subject during exercise. The method comprises: determining a phase shift of the input radiofrequency signals relative to the output radiofrequency signals; calculating cardiac output based on the phase shift; and using the cardiac output for estimating the exercise capacity of the subject.

According to some embodiments of the invention, the method further comprising obtaining at least one CPX measure pertaining to a cardiopulmonary exercise testing, and combining the cardiac output with the at least one CPX measure to estimate the exercise capacity of the subject.

According an aspect of the present invention there is provided a method of estimating exercise capacity of a subject. The method comprises: transmitting output radiofrequency signals to the subject during exercise; receiving input radiofrequency signals from the subject during exercise; and executing a method for estimating exercise capacity of a subject.

According to some embodiments of the invention, the method further comprises reducing or eliminating amplitude modulation of the input radiofrequency signals so as to provide input radiofrequency signals of substantially constant envelope.

According to some embodiments of the invention the method further comprises mixing the output radiofrequency signals and the input radiofrequency signals so as to provide a mixed radiofrequency signal, and filtering out a portion of the mixed radiofrequency signal so as to substantially increase a signal-to-noise ratio of a remaining portion of the mixed radiofrequency signal.

According to some embodiments of the invention, the method further comprises performing a cardiopulmonary exercise testing to provide at least one CPX measure and combining the cardiac output with the at least one CPX measure to estimate the exercise capacity of the subject.

According to some embodiments of the invention, the method further comprises applying a dynamically variable filter.

According an aspect of the present invention there is provided apparatus for estimating exercise capacity of a subject using output radiofrequency signals transmitted to the subject during exercise and input radiofrequency signals received from the subject during exercise. The apparatus comprises: a phase shift determinator configured for determining a phase shift of the input radiofrequency signals relative to the output radiofrequency signals; a cardiac output calculator configured for calculating cardiac output based on the phase shift;

and an exercise capacity estimator configured for using the cardiac output for estimating the exercise capacity of the subject.

According to some embodiments of the invention the exercise capacity estimator is configured for combining the cardiac output with at least one CPX measure to estimate the exercise capacity of the subject.

According to an aspect of the present invention there is provided a system for estimating exercise capacity of a subject. The system comprises comprising: a radiofrequency generator for generating output radiofrequency signals; a plurality of electrodes designed for transmitting the output radiofrequency signals to the subject and for sensing input radiofrequency signals from the subject; and an apparatus for estimating exercise capacity of a subject.

According to some embodiments of the invention, the system further comprises a cardiopulmonary exercise testing system configured to provide at least one CPX measure, wherein the exercise capacity estimator is configured for combining the cardiac output with at least one CPX measure to estimate the exercise capacity of the subject.

According to some embodiments of the invention, the apparatus further comprises an envelope elimination unit designed and configured for reducing or eliminating amplitude modulation of the input radiofrequency signals so as to provide input radiofrequency signals of substantially constant envelope.

According to some embodiments of the invention the apparatus further comprises a mixer configured for mixing the output radiofrequency signals and the input radiofrequency signals, to provide a mixed radiofrequency signal; and a radiofrequency filter for filtering out a portion of the mixed radiofrequency signal so as to substantially increase a signal-to-noise ratio of a remaining portion of the mixed radiofrequency signal.

According to some embodiments of the invention the apparatus further comprises a filtering unit configured for filtering the input signals using dynamically variable filter.

According to some embodiments of the invention the cardiac output is calculated using a linear relationship between the phase shift and the cardiac output.

According to some embodiments of the invention the dynamically variable filter is adapted in response to a change in a physiological condition of the subject.

According to some embodiments of the invention the physiological condition is a heart rate of the subject.

According to some embodiments of the invention a lower frequency bound characterizing the filter is about $0.9*(HR/60)$ Hz at all times, wherein the HR is the heart rate in units of beats per minute.

According to some embodiments of the invention an upper frequency bound characterizing the filter is about $6+1.5*[(HR/60)-1]$ Hz at all times, wherein the HR is the heart rate in units of beats per minute.

According to some embodiments of the invention the CPX measure(s) comprises ratio of ventilation efficiency to carbon dioxide production rate.

According to some embodiments of the invention the CPX measure(s) comprises oxygen uptake efficiency slope.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
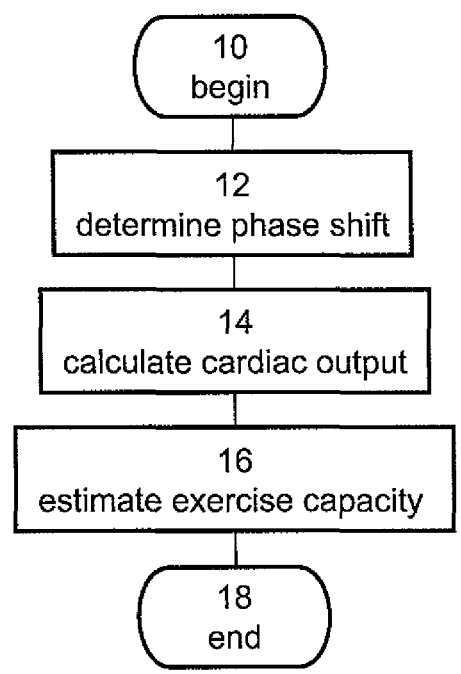
FIG. 1 is a flowchart diagram of a method suitable for estimating exercise capacity of a subject according to various exemplary embodiments of the present invention.

The present invention, in some embodiments thereof, relates to medical application and, more particularly, but not exclusively, to a method and system for estimating exercise capacity.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Computer programs implementing the method according to embodiments of the present invention can commonly be distributed to users on a distribution medium such as, but not limited to, a floppy disk, CD-ROM and flash memory cards. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

Referring now to the drawings, FIG. 1 is a flowchart diagram of a method suitable for estimating exercise capacity of a subject according to various exemplary embodiments of the present invention.

It is to be understood that, unless otherwise defined, the method steps described hereinbelow can be executed either contemporaneously or sequentially in many combinations or orders of execution. Specifically, the ordering of the flowcharts diagrams is not to be considered as limiting. For example, two or more method steps, appearing in the following description or in the flowchart diagrams in a particular order, can be executed in a different order (e.g., a reverse order) or substantially contemporaneously. Additionally, several method steps described below are optional and may not be executed.

The method is particularly useful for estimating the exercise capacity from output radiofrequency signals transmitted to the subject during exercise and input radiofrequency signals received from the subject during exercise.

The method begins at step 10 and continues to step 12 in which a phase shift of the input radiofrequency signals relative to the output radiofrequency signals is determined. The method continues to step 14 in which a cardiac output is calculated, based on the phase shift. The method continues to step 16 in which the cardiac output is used for estimating the exercise capacity of the subject.

The method ends at step 18.

Figure 2:
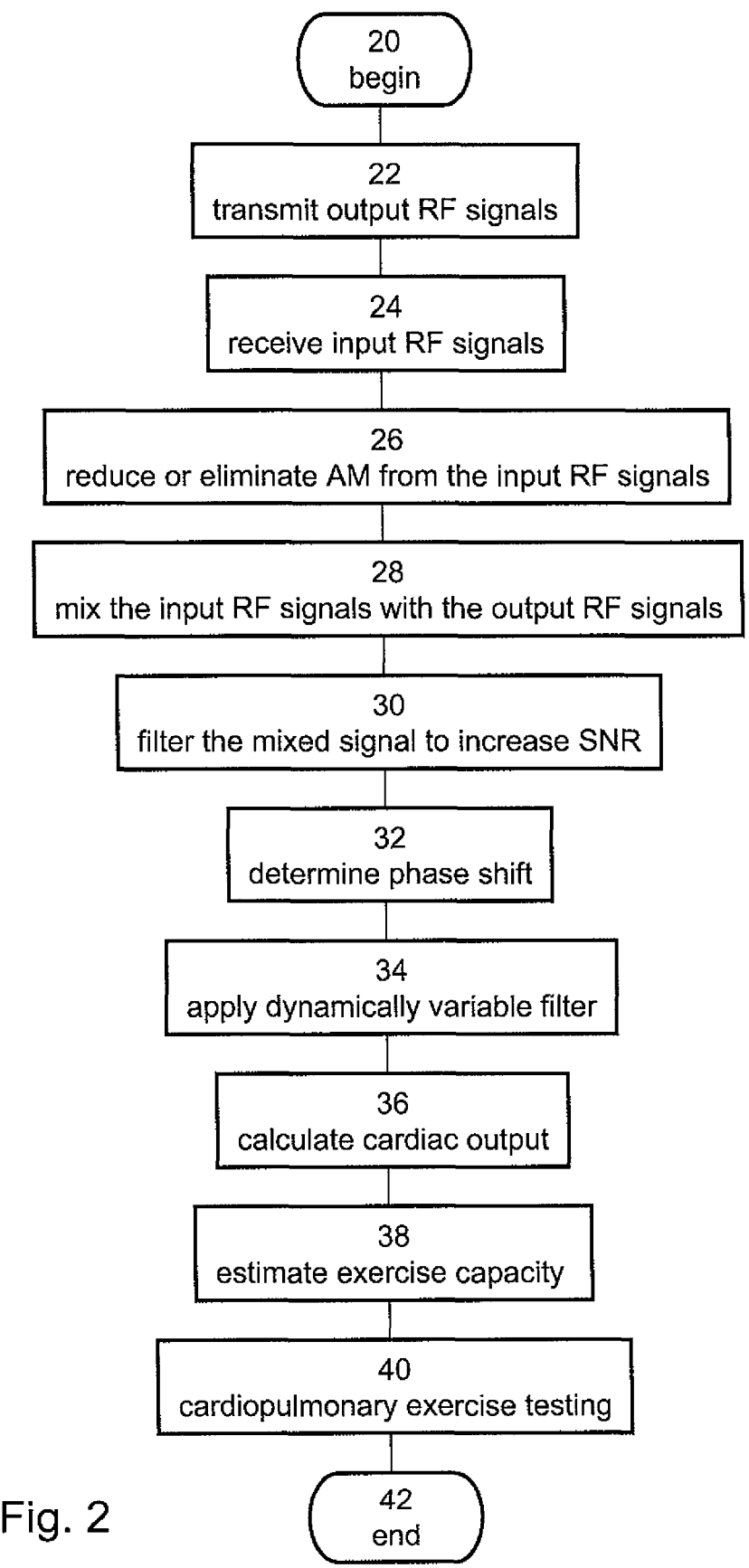
FIG. 2 is a flowchart diagram of a more detailed method suitable for estimating exercise capacity of a subject according to various exemplary embodiments of the present invention.

A more detailed method for estimating exercise capacity of a subject according to some embodiments of the present invention is illustrated in the flowchart diagram of FIG. 2.

The method begins at step 20 and optionally continues to step 22 in which output radiofrequency signals are transmitted to the subject during exercise, and step 24 in which input radiofrequency signals are received from the subject during exercise. The output radiofrequency signals can be generated by a radiofrequency generator which generates a periodic high frequency current output in response to a periodic control input signal. The current output can be transmitted to the subject via an arrangement of electrodes for carrying current output from the radiofrequency generator as known in the art. The electrodes can be connected to locations of the body of the subject, e.g., above and below the heart. Since the transmission and reception of signals is done during exercise, the electrodes are optionally and preferably placed on the subject's back so as not to interfere with upper body motion.

Current, generated by the radiofrequency generator, flows across the thorax and causes a voltage drop due to the impedance of the body. The input radiofrequency signals are typically, but not obligatorily, relate to the hemodynamic reactance of an organ of the subject.

As used herein, "hemodynamic reactance" refers to the imaginary part of the impedance. Techniques for extracting the imaginary part from the total impedance are known in the art. Typically, such extraction is performed at hardware level but the use of algorithm at a software level is not excluded from the scope of the present invention.

According to some embodiments of the present invention the method continues to step 26 in which amplitude modulation of the input radiofrequency signals is reduces or, more preferably, eliminated. Optionally and preferably the phase modulation of the signals is maintained. The input radiofrequency signals typically carry a substantial amount of AM noise, which can be described, without limitation as a signal $v(t)\cos(\omega t+\phi(t))$, which contains both phase and amplitude modulation. According to some embodiments the method generates signals having a substantial constant envelope, e.g., $v_0 \cos(\omega t+\phi(t))$, where $v_0$ is substantially a constant. The obtained signals thus represent the phase (or frequency) modulation of the input radiofrequency signal. The reduction or elimination of the amplitude modulation can be achieved, for example, using a limiter amplifier which amplifies the radiofrequency signals and limits their amplitude such that the amplitude modulation is removed.

In some embodiments, the method proceeds to step 28 in which the output radiofrequency signals are mixed with the input radiofrequency signals so as to provide a mixed radiofrequency signal. According to a preferred embodiment of the present invention, the mixed radiofrequency signal is composed of a plurality of radiofrequency signals, which may be, in one embodiment, a radiofrequency sum and a radiofrequency difference. A sum and a difference may be achieved, e.g., by multiplying the input and output signals. Since a multiplication between two frequencies is equivalent to a frequency sum and a frequency difference, the mix signal is composed of the desired radiofrequency sum and radiofrequency difference.

One ordinarily skilled in the art would appreciate that the advantage in the production of a radiofrequency sum and a radiofrequency difference is that whereas the radiofrequency sum includes both the signal and a considerable amount of electrical noise, the radiofrequency difference is approximately noise-free.

According to a preferred embodiment of the method continues to step 30 in which a portion of the mixed signal is filtered out such that a remaining portion of the mixed signal is characterized by a signal-to-noise ratio (SNR) which is substantially higher compared to the signal-to-noise ratio of the mixed signal or input radiofrequency signal.

The method continues to step 23 in which a phase shift $\Delta\phi$ of the input radiofrequency signals relative to the output radiofrequency signals is determined. It was found by the inventors of the present invention that the phase shift of the input signals, as received from the subject, relative to the output signals as generated by the radiofrequency generator, is indicative of the cardiac output of the subject.

The advantage of using $\Delta\phi$ for determining the cardiac output is that the relation between the blood flow and $\Delta\phi$ depends on fewer measurement-dependent quantities as compared to conventional determination techniques in which the impedance is used. The phase shift can be determined for any frequency component of the spectrum of radiofrequency signals received from the organ. For example, in one embodiment, the phase shift is preferably determined from the base frequency component, in another embodiment the phase shift is preferably determined from the second frequency component, and so on. Alternatively the phase shift can be determined using several frequency components, e.g., using an appropriate averaging algorithm.

In some embodiments of the present invention the method continues to step 34 in which a dynamically variable filter is applied. The dynamically variable filter filters the data according to a frequency band which is dynamically adapted in response to a change in the physiological condition of the subject. It was found by the Inventor of the present invention that the dynamical adaptation of the frequency band to the physiological condition of the subject can significantly reduce the influence of unrelated signals on the measured property.

Thus, in the present embodiment, step 34 includes a process in which first the physiological condition of the subject is determined, then a frequency band is selected based on the physiological condition of the subject, and thereafter the input signals are filtered according to frequency band. The frequency band is dynamically adapted in response to a change in the physiological condition.

The physiological condition is preferably, but not obligatorily, the heart rate of the subject. The data pertaining to the physiological condition can be collected via a suitable data collection unit either in analog or digital form, as desired. For example, the physiological condition can be a heart rate which can be determined, e.g., by analysis of ECG signals or the like.

While the embodiments below are described with a particular emphasis to physiological condition which is a heart rate, it is to be understood that more detailed reference to the heart rate is not to be interpreted as limiting the scope of the invention in any way. For example, in exemplary embodiments of the present invention the physiological condition is a ventilation rate of the subject, a repetition rate of a particular muscle unit and/or one or more characteristics of an action potential sensed electromyography.

The adaptation of the frequency band to the physiological condition can be according to any adaptation scheme known in the art. For example, one or more parameters of the frequency band (e.g., lower bound, upper bound, bandwidth, central frequency) can be a linear function of a parameter characterizing the physiological condition. Such parameter can be, for example, the number of heart beats per minute.

Figure 3A:
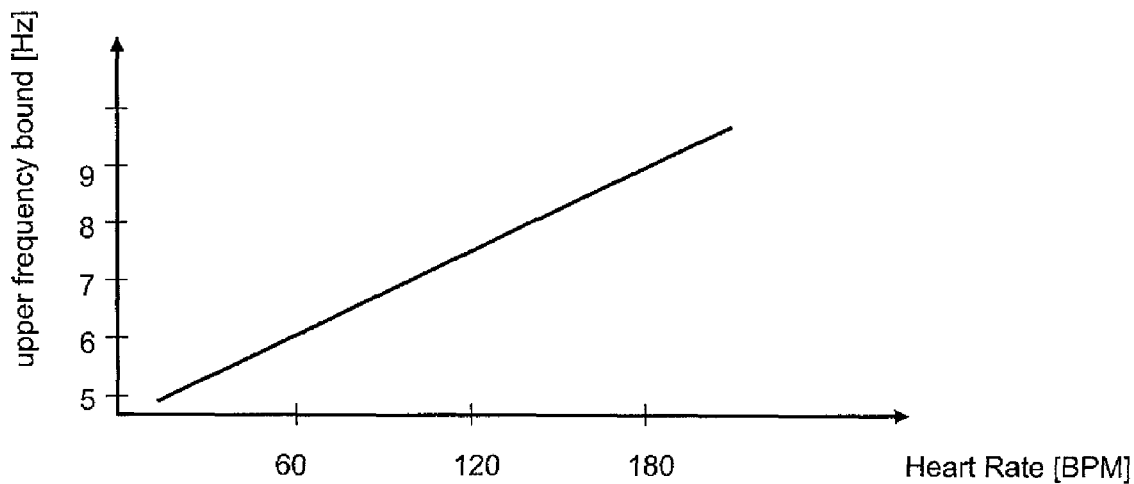
FIGS. 3a-b show a representative example of dynamically varying frequency bounds, employed according to embodiments of the present invention.
Figure 3B:
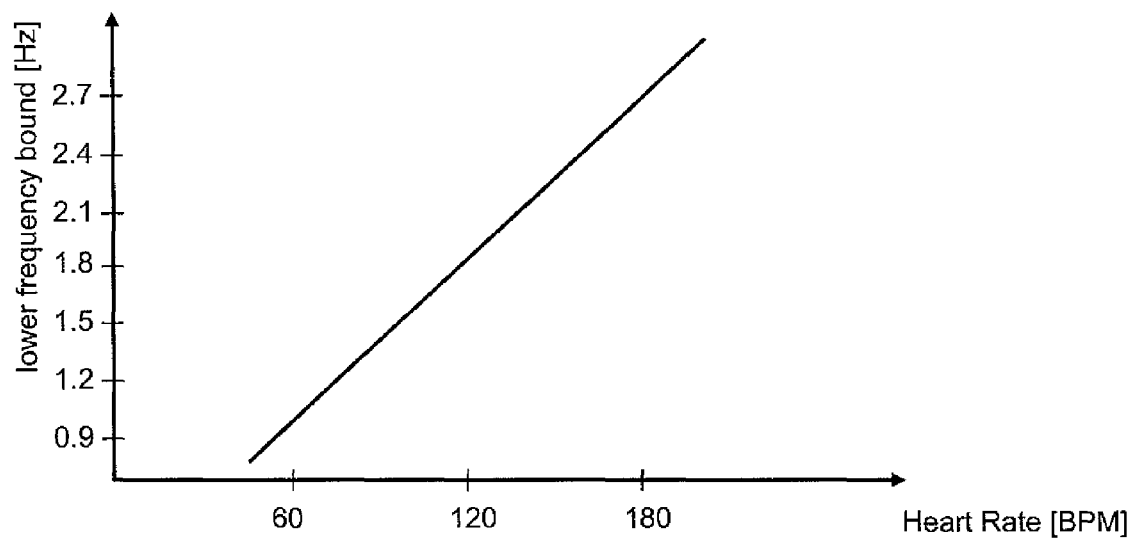

A representative example of a dynamically varying frequency bounds is illustrated in FIGS. 3*a-b*. Shown in FIGS. 3*a-b* is the functional dependence of the frequency bounds (upper bound in FIG. 3*a* and lower bound in FIG. 3*b*) on the heart rate of the subject. As shown in FIG. 3*a*, the upper bound of the frequency band varies linearly such that at a heart rate of about 60 beats per minute (bpm) the upper bound is about 6 Hz, and at a heart rate of about 180 bpm the upper bound is about 9 Hz. Preferably, the upper bound is about $6+1.5\times[(HR/60)-1]$ Hz at all times, where HR is the heart rate of the subject in units of bpm. As shown in FIG. 3*b*, the lower bound of the frequency band varies linearly such that at a heart rate of about 60 the lower bound is about 0.9 Hz bpm and at a heart rate of about 180 bpm the lower bound is about 2.7 Hz. The lower bound is about $0.9\times(HR/60)$ Hz at all times.

As used herein the term "about" refers to ±10%.

Figure 3C:
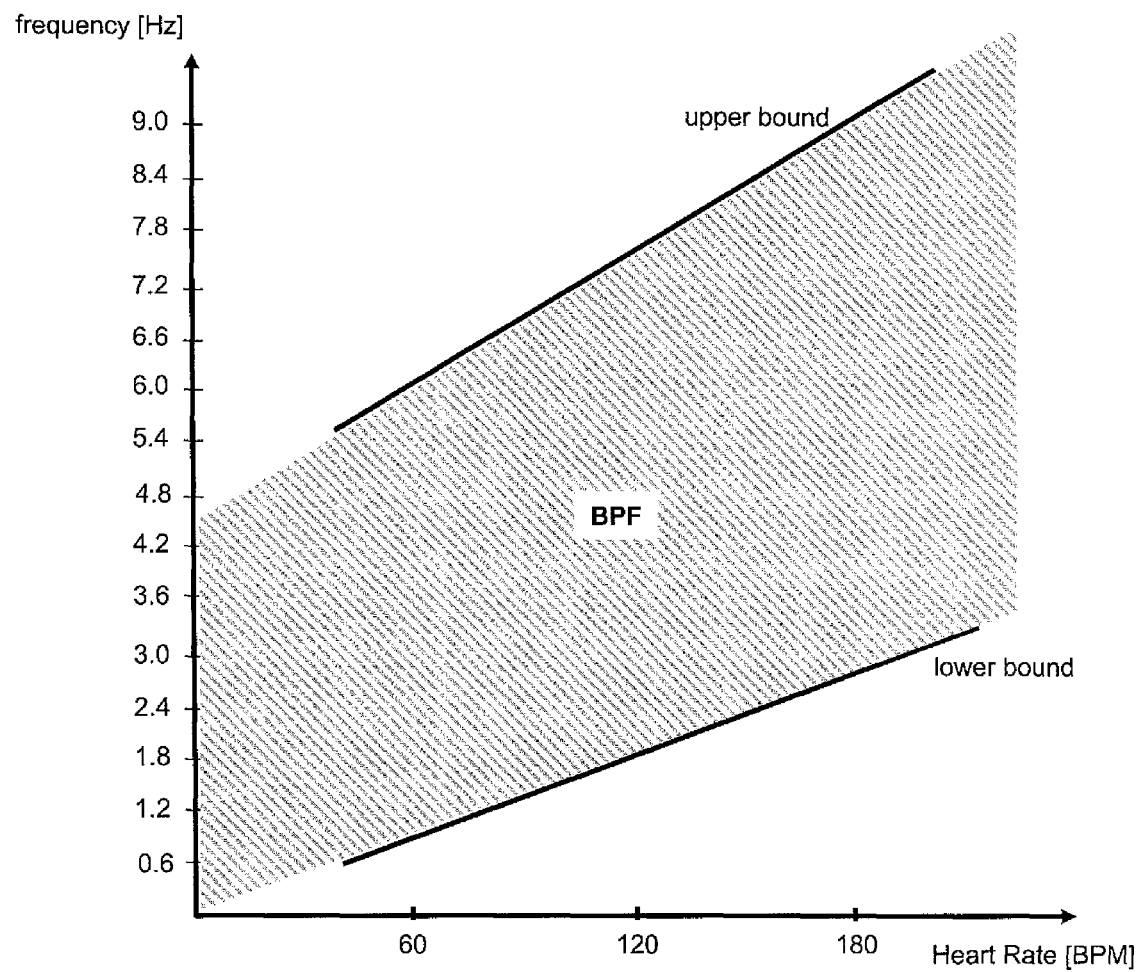
FIG. 3c show a representative example of a dynamically varying frequency band, employed according to embodiments of the present invention.

A dynamically varying band pass filter (BPF) characterized by the frequency bounds described above is illustrated in FIG. 3*c*. As shown, each heart rate is associated with a frequency band defined by a lower bound and an upper bound. For example, for a heart rate of 60 bpm, FIG. 3*c* depicts a BPF in which the lower bound is about 0.9 Hz and the upper bound is about 6 Hz.

It is to be understood that the values presented above and the functional relations illustrated in FIGS. 3*a-b* are exemplary embodiments and should not be considered as limiting the scope of the present invention in any way. In other exemplary embodiments, the functional relations between the frequency band and the physiological condition can have different slopes and/or offsets, or they can be non-linear.

The method continues to step 36 in which the cardiac output is calculated, based on $\Delta\phi$. It was found by the inventor of the present invention that there is a linear relationship between $\Delta\phi$ and the cardiac output, with a proportion coefficient comprising the systolic ejection time, T. For example, the cardiac output CO can be calculated using the relation CO=const.$\times T\times\Delta\phi\times HR$, where HR is the heart rate of the subject (e.g., in units of beats per minutes), and "const." is a constant which can be found, for example, using a calibration curve.

The method continues to step 38 in which the calculated cardiac output is used for estimating the exercise capacity of the subject. Generally, the exercise capacity correlates with the cardiac output. For example, when the cardiac output is below a predetermined threshold, the method can estimate that the subject's exercise capacity is low, and when the cardiac output is above a predetermined threshold, the method can estimate that the subject's exercise capacity is high. It was demonstrated by the present inventors that during exercise the cardiac output among normal subjects is about 34% higher than that of CHF patients. The method of the present embodiments can therefore be used to assess or determine worsening of the condition of the subject, particularly subjects with congestive heart failure.

In some embodiments of the present invention, the method continues to step 40 in which a cardiopulmonary exercise testing is performed to provide one or more CPX. The cardiac output can be combined with the CPX measure(s) and the combination can be used to estimate the exercise capacity, and/or to assess the quality of the estimation. For example, as demonstrated in the Examples section that follows, the maximal cardiac output is inversely correlated to the $VE/VCO_2$ slope, where VE is the ventilation efficiency and $VCO_2$ is the carbon dioxide production rate. The correlation coefficient between the maximal cardiac output during exercise and the $VE/VCO_2$ slope can be calculated and the quality of the exercise capacity estimation can be assessed based on this correlation coefficient, where negative and large in absolute value correlation coefficient corresponds to high quality of exercise capacity estimation and vice versa.

It is further demonstrated in the Examples section that follows that the maximal cardiac output is directly correlated to the oxygen uptake efficiency slope OUES. The correlation coefficient between the maximal cardiac output during exercise and the OUES can be calculated and the quality of the exercise capacity estimation can be assessed based on this correlation coefficient, where high positive correlation coefficient corresponds to high quality of exercise capacity estimation and vice versa.

The method ends at step 42.

Figure 4:
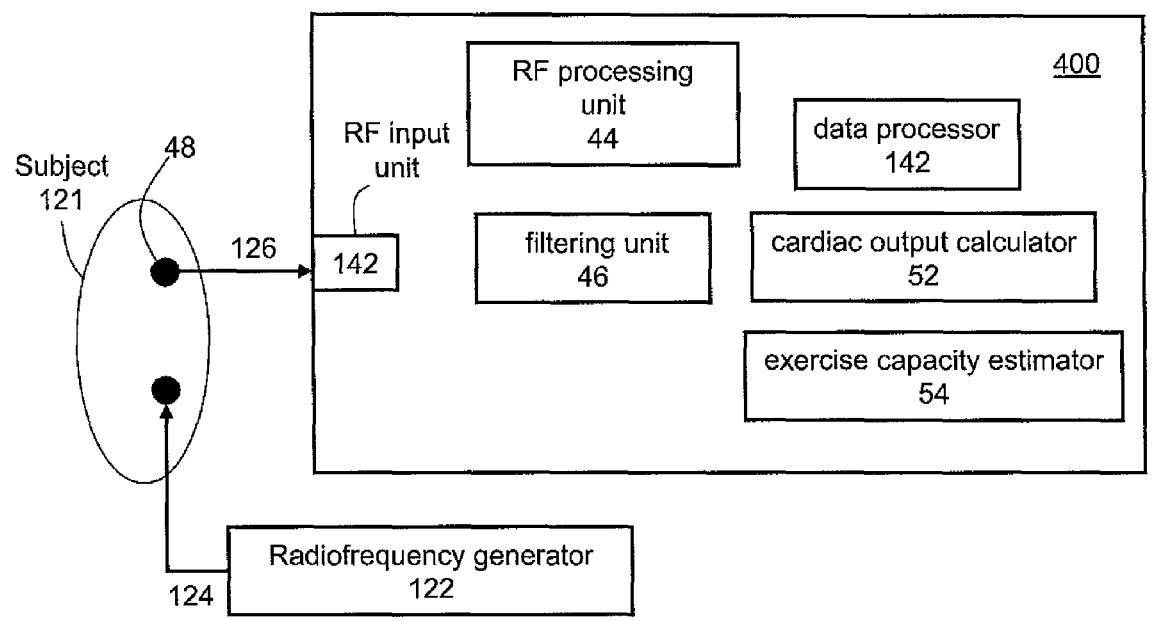
FIG. 4 is a schematic illustration of apparatus for estimating exercise capacity of a subject, according to various exemplary embodiments of the present invention.

Reference is now made to FIG. 4 which is a schematic illustration of apparatus 400 for estimating exercise capacity of a subject 121, according to various exemplary embodiments of the present invention.

Apparatus 400 comprises an input unit 142 for receiving input radiofrequency signals sensed from the organ. The input radiofrequency signals typically comprise radiofrequency signals related to the electrical properties of the organ (e.g., bioimpedance which may generally relate to the impedance and/or hemodynamic reactance of the organ). The signals are sensed from one or more sensing locations 48 on the organ of subject 121 and are originated by output radiofrequency signals 124 generated by a radiofrequency generator 122.

Apparatus 400 further comprises a signal processing unit 44 which processes the input radiofrequency signals. The processing may include, for example, mixing, demodulation, determination of phase shift, analog filtering, sampling and any combination thereof. Signal processing unit 44 may or may not be in communication with radiofrequency generator 122, as desired. A representative example of signal processing unit 44 is provided hereinunder with reference to FIG. 5.

Apparatus 400 is optionally and preferably designed for determining a phase shift $\Delta\phi$ of signals 126 relative to signals 124. This can be done using a phase shift determinator 50 (not shown, see FIG. 5) which can operate according to any known technique for determining a phase shift. The phase shift can be determined for any frequency component of the spectrum of radiofrequency signals received from the organ. For example, in one embodiment, the phase shift is determined from the base frequency component, in another embodiment the phase shift is determined from the second frequency component, and so on. Alternatively the phase shift can be determined using several frequency components, e.g., using an appropriate averaging algorithm.

The input radiofrequency signals may include one or more noise components, which may be introduced into the signal due to various reasons, e.g., subject agitation or breathing. In various exemplary embodiments of the invention apparatus 400 is capable of reducing or eliminating these noise components. In some embodiments of the present invention apparatus 400 further comprises a filtering unit 46 which filters the processed input signals. Unit 46 preferably performs the filtration operation in the frequency domain. Thus, in various exemplary embodiments of the invention, a series of samples of the processed radiofrequency signals are transformed, e.g., by a Fast Fourier Transform (FFT), to provide a spectral decomposition of the signals in the frequency domain. The transformation to the frequency domain can be done by a data processor. Algorithms for performing such transformations are known to those skilled in the art of signal processing.

The obtained spectral decomposition of the signal is filtered by unit 46 which typically eliminates one or more of the frequencies in the spectrum, depending on the upper and lower frequency bounds of the filter employed by unit 46. Unit 46 preferably employs a dynamically variable filter, such as, but not limited to, the dynamically variable filer described hereinabove.

In some embodiments of the present invention apparatus 400 comprises a cardiac output calculator 52 which calculates the cardiac output and an exercise capacity estimator 54 which uses the calculated cardiac output for estimating the exercise capacity of the subject as further detailed hereinabove. In some embodiments, exercise capacity estimator 54 combines the calculated cardiac output with one or more CPX measures, e.g., by means of performing statistical analysis. Cardiac output calculator 52 and exercise capacity estimator 54 can be associated with a data processor 142. Data processor 142 can also be employed by unit 46 for performing the transformation to the frequency domain and/or eliminating the frequency components according to the dynamically variable frequency bounds.

Data processor 142 can also be configured for calculating other quantities, e.g., stroke volume and/or other blood-volume related quantities.

Figure 5:
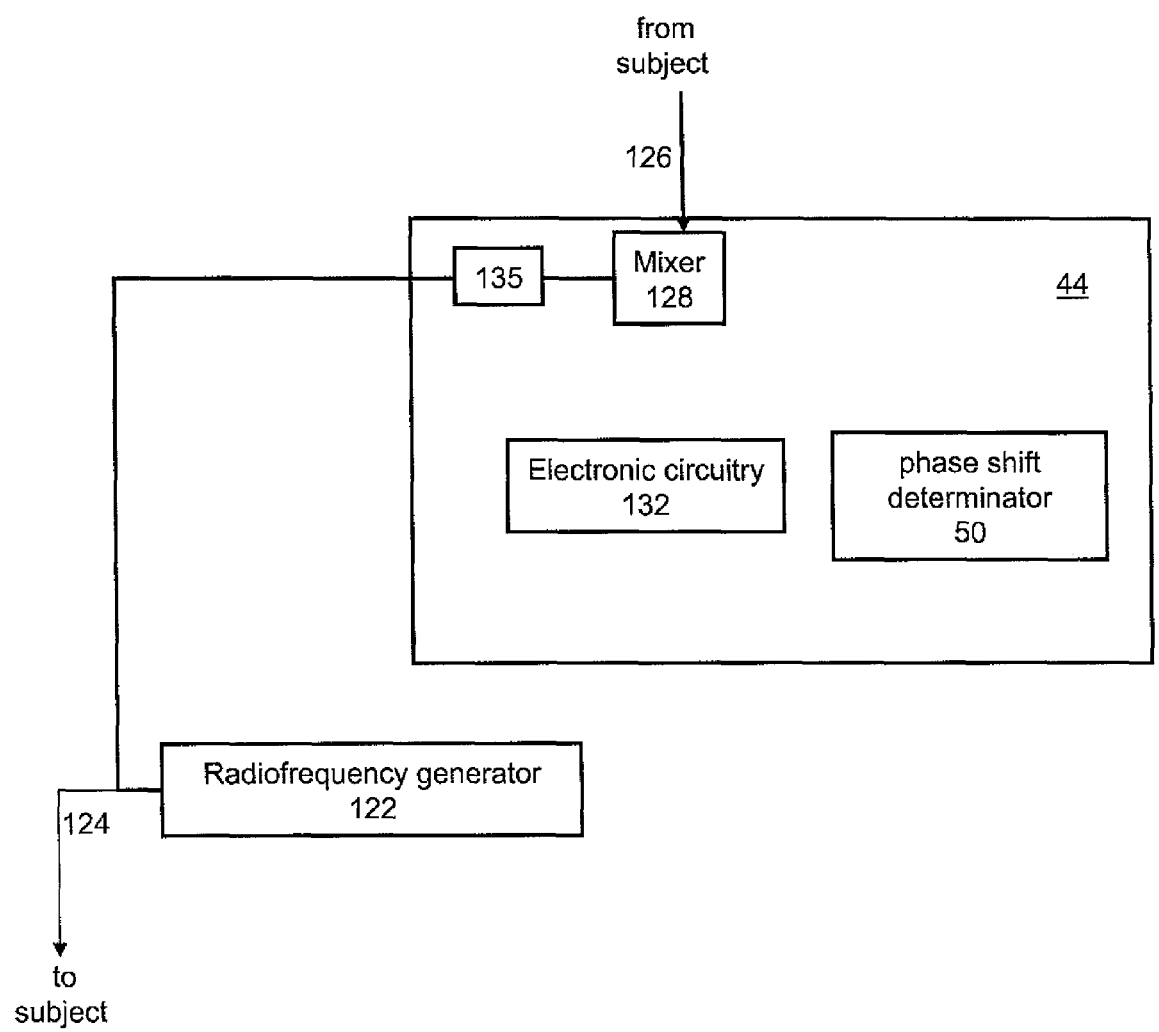
FIG. 5 is a schematic illustration of a signal processing unit, according to various exemplary embodiments of the present invention.

Reference is now made to FIG. 5 which schematically illustrates signal processing unit 44, according to various exemplary embodiments of the present invention. Unit 44 preferably comprises a mixer 128, electrically communicating with generator 122, for mixing output signals 124 and input signals 126, so as to provide a mixed radiofrequency signal. Signals 124 and 126 may be inputted into mixer 128 through more than one channel, depending on optional analog processing procedures (e.g., amplification) which may be performed prior to the mixing.

Mixer 128 may be any known radiofrequency mixer, such as, but not limited to, double-balanced radiofrequency mixer and unbalanced radiofrequency mixer. According to a preferred embodiment of the present invention, the mixed radiofrequency signal is composed of a plurality of radiofrequency signals, which may be, in one embodiment, a radiofrequency sum and a radiofrequency difference. A sum and a difference may be achieved, e.g., by selecting mixer 128 such that signals 124 and signals 126 are multiplied thereby. Since a multiplication between two frequencies is equivalent to a frequency sum and a frequency difference, mixer 128 outputs a signal which is composed of the desired radiofrequency sum and radiofrequency difference.

According to various exemplary embodiments of the present invention unit 44 further comprises a phase shift determinator 50 for determining the phase shift of the input signals relative to the output signal. Phase shift determinator 50 can determine the phase shift according to any technique known in the art. For example, the phase shift can be determined from the radiofrequency difference outputted from mixer 128.

According to a preferred embodiment of the present invention processing unit 44 further comprises electronic circuitry 132, which filters out a portion of the signal such that a remaining portion of the signal is characterized by a substantially increased signal-to-noise ratio.

Figure 6:
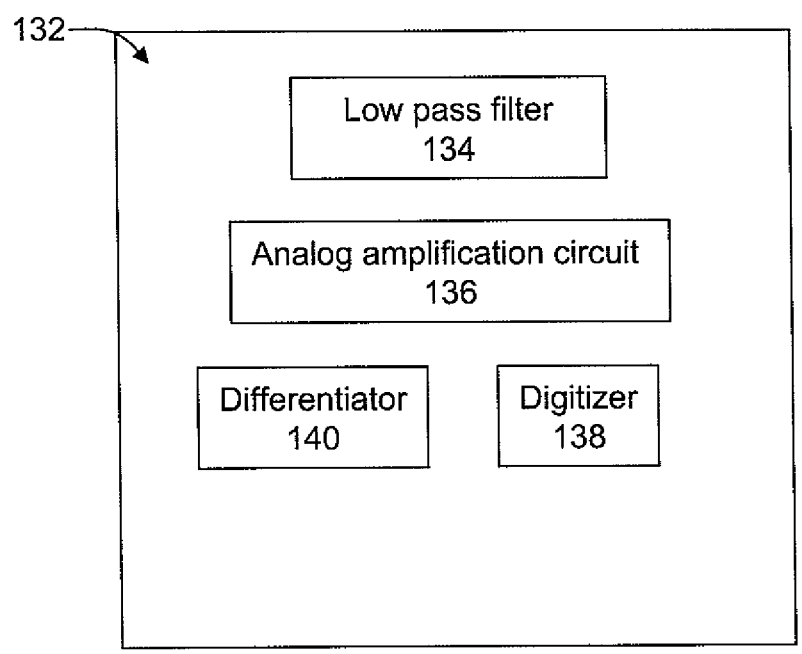
FIG. 6 is a block diagram of electronic circuitry, according to various exemplary embodiments of the present invention.

Circuitry 132 is better illustrated in FIG. 6. According to an embodiment of the present invention circuitry 132 comprises a low pass filter 134 to filter out the high frequency content of the signal. Low pass filter 134 is particularly useful in the embodiment in which mixer 128 outputs a sum and a difference, in which case low pass filter 134 filters out the radiofrequency sum and leaves the approximately noise-free radiofrequency difference. Low pass filter 134 may be designed and constructed in accordance with the radiofrequency difference of a particular system which employs apparatus 400. A judicious design of filter 134 substantially reduces the noise content of the remaining portion.

Circuitry 132 preferably comprises an analog amplification circuit 136 for amplifying the remaining portion of the signal. The construction and design of analog amplification circuit 136 is not limited, provided circuit 136 is capable of amplifying the signal. Amplification circuits suitable for the present embodiments are found in International Patent Application, Publication Nos. WO 2004/098376 and WO 2006/087696 the contents of which are hereby incorporated by reference.

According to a preferred embodiment of the present invention circuitry 132 further comprises a digitizer 138 for digitizing the signal. The digitization of the signal is useful for further digital processing of the digitized signal, e.g., by a microprocessor.

Optionally, circuitry comprises a differentiator 140 (either a digital differentiator or an analog differentiator) for performing at least one time-differentiation of the measured impedance to obtain a respective derivative (e.g., a first derivative, a second derivative, etc.) of the bioimpedance or hemodynamic reactance. Differentiator 140 may comprise any known electronic functionality (e.g., a chip) that is capable of performing analog or digital differentiation.

According to a preferred embodiment of the present invention signal processing unit 44 comprises an envelope elimination unit 135 which reduces or, more preferably, eliminates amplitude modulation of signals 126. Optionally and preferably, unit 135 maintains the phase modulation of signals 126. The output of unit 135 represents the phase (or frequency) modulation of signal 126, as further detailed hereinabove. Unit 135 can employ, for example, a limiter amplifier which amplifies signals 126 and limits their amplitude such that the amplitude modulation is removed. The advantage of the removal of the amplitude modulation is that it allows a better determination of the phase shift $\Delta\phi$ between the input and output signals, as further detailed hereinabove.

Figure 7:
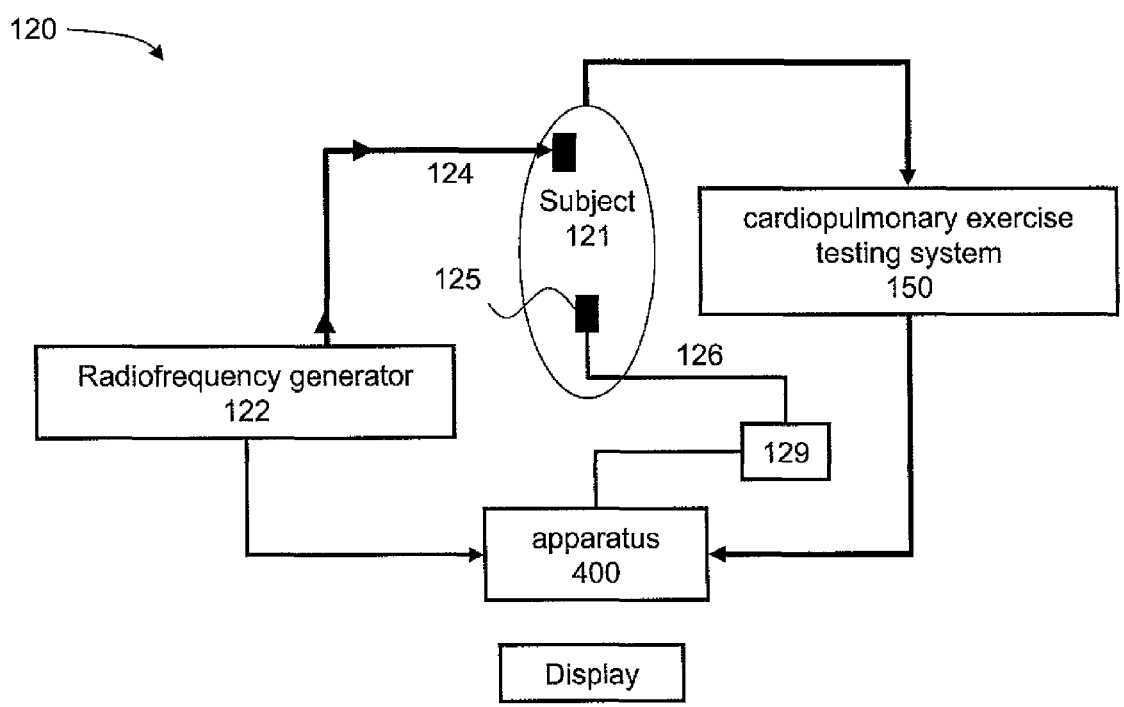
FIG. 7 is a schematic illustration of a system for estimating exercise capacity of a subject.

Reference is now made to FIG. 7, which is a schematic illustration of system 120 for estimating exercise capacity of a subject, according to a preferred embodiment of the present invention. System 120 preferably comprises a radiofrequency generator 122, for generating output radiofrequency signals. Generator 122 may be embodied as any radiofrequency generator. System 120 further comprises a plurality of electrodes 125, which are connected to the skin of subject 121. Electrodes 125 transmit output radiofrequency signals 124, generated by generator 122 and sense input radiofrequency signals 126 originated from the organ of subject 121.

System 120 preferably comprises any of the components of apparatus 400 described above. According to a preferred embodiment of the present invention system 120 further comprises a detector 129 for detecting a voltage drop on a portion of the body of subject 121 defined by the positions of electrodes 125. In response to the detected voltage, detector 129 preferably generates signals which are indicative of impedance of the respective portion of the body. In this embodiment, the stroke volume can be calculated using $(dX/dt)_{max}$, as further detailed hereinabove. Knowing the stroke volume, the cardiac output is calculated by multiplying the stroke volume by the heart rate of the subject. More preferably, detector 129 generates signals which are indicative of a hemodynamic reactance, X.

In some embodiments, system 120 comprises a cardiopulmonary exercise testing system 150 which provides apparatus 400 with one or more CPX measure via a communication line 152. Apparatus 400 combines the calculated cardiac output with the CPX measure(s) for estimating the exercise capacity as further detailed hereinabove.

Following are technical preferred values which may be used for selective steps and parts of the embodiments described above.

The output radiofrequency signals are preferably from about 10 KHz to about 200 KHz in frequency and from about 10 mV to about 200 mV in magnitude; the input radiofrequency signals are preferably about 75 KHz in frequency and about 20 mV in magnitude; a typical impedance which can be measured by the present embodiments is from about 5 Ohms to about 75 Ohms; the resulting signal-to-noise ratio of the present embodiments is at least 40 dB; low pass filter 134 is preferably characterized by a cutoff frequency of about 35 Hz and digitizer 138 preferably samples the signals at a rate of about 500-1000 samples per second.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following example.

EXAMPLES

Reference is now made to the following example, which together with the above descriptions illustrates some embodiments of the invention in a non limiting fashion.

Some embodiments of the present invention were utilized for the purpose of estimating the exercise capacity of subjects.

Methods

Subjects

Data obtained from 36 consecutive subjects referred to a private cardiology clinic for CPX testing for evaluation of dyspnea. All patients provided consent for the use of their data in the analysis. Twenty three of the subjects had heart failure (18 with low EF, 5 with normal EF) and 13 were ultimately diagnosed as normal (normal EF and peak $VO_2$, dyspnea based on noncardiac factors). Demographic and clinical characteristics of the subjects are summarized in Table 1.

TABLE 1

| Patient Characteristics | CHF | Normal | p |
|---|---|---|---|
| N | 23 | 13 | |
| Age (years) | 66.6 ± 10 | 51.0 ± 11 | <0.001 |
| Height (cm) | 176 ± 10 | 172 ± 10 | 0.20 |
| Weight (kg) | 87.0 ± 15 | 76.1 ± 15 | 0.04 |
| Ejection Fraction (%) | 35.9 ± 13 | 56.5 ± 9.2 | 0.003 |
| Peak $VO_2$ (ml/kg/min) | 14.7 ± 5.4 | 24.8 ± 6.2 | <0.001 |
| CHF Etiology, # subjects (%) | | | |
| Ischemic Cardiomyopathy | 17 (74) | — | — |
| Idiopathic Dilated Cardiomyopathy | 1 (4) | — | — |
| CHF with Normal EF* | 4 (17) | — | — |
| NYHA Classification, # (%) | | — | — |
| Class I | 1 (5) | — | — |
| Class II | 3 (15) | — | — |
| Class III | 13 (65) | — | — |
| Class IV | 3 (15) | — | — |
| Medications, # subjects (%) | | | |
| Digoxin | 3 (13) | 0 (0) | — |
| Beta Blocker | 22 (96) | 6 (46) | 0.05 |
| ACE/ARB | 17 (74) | 5 (38) | 0.05 |

CHF = chronic heart failure;
EF = ejection fraction;
NYHA = New York Heart Association;
ACE/ARB = ACE inhibitor/angiotensin receptor blocker;
*>45%

In the overall population there was a broad range of EFs, peak $VO_2$ values and peak cardiac outputs. All subjects were limited during exercise by fatigue or dyspnea, and none had clinical evidence of pulmonary disease or ischemic changes on the ECG.

Exercise Testing

Symptom limited maximal exercise tests were performed on a treadmill using a ramp protocol [Myers J, Buchanan N, Walsh D, Kraemer M, McAuley P, Hamilton-Wessler M, Froelicher V F. Comparison of the ramp versus standard exercise protocols, *J Am Coll Cardio* 1991; 17:1334-1342].

All subjects were requested to abstain from eating or smoking at least 3 hours prior to the test. Ventilatory oxygen uptake was measured using a Medical Graphics Corporation (CPX-D, St. Paul, Minn.). Gas exchange data were acquired breath-by-breath and expressed in ten second intervals of rolling 30 second averages. Oxygen uptake, carbon dioxide production, minute ventilation and respiratory exchange ratio were calculated on-line. The percentage of age-predicted normal peak $VO_2$ was determined for each patient using the equation of Wasserman et al. [Wasserman K, Hansen J E, Sue D Y, Casaburi R, Whipp B J. Principles of exercise testing and interpretation, $4^{th}$ ed. Baltimore: Lippincott, Williams & Wilkins, 2004]. Estimated peak $VO_2$ was determined from the American College of Sports Medicine equations [American College of Sports Medicine. Guidelines on Exercise Testing and Prescription, $7^{th}$ ed. Baltimore: Lippincott, Williams & Wilkins, 2006]. A 12-lead electrocardiogram was monitored continuously and recorded every minute. Blood pressure was recorded manually every two minutes throughout the test.

All subjects were encouraged to provide a maximal effort; among patients with CHF, the Borg 0 to 10 perceived exertion scale was used to quantify effort [Borg GAV. Borg's perceived exertion scales, Champaign: Human Kinetics, 1998]. The ventilatory threshold was determined by two experienced, independent reviewers using the V-slope method [Beaver W L, Wasserman K, Whipp B J. A new method for detecting the anaerobic threshold by gas exchange. J Appl Physiol 1986; 60:2020-2027] and confirmed by ventilatory criteria. Ventilatory efficiency (VE) and $VCO_2$ responses, acquired from the initiation of exercise to peak, were used to calculate a $VE/VCO_2$ slope via least squares linear regression. Oxygen uptake efficiency slope (OUES) was derived by the slope of a semi-log plot of minute ventilation versus $VO_2$. As such, the OUES is an estimation of the efficiency of ventilation with respect to $VO_2$, with greater slopes indicating greater ventilatory efficiency.

Cardiac Output

Cardiac output was determined using a NICOM system (Cheetah Medical, Wilmington, Del.) disclosed in WO 2006/087696 and supplemented by a dynamically variable filter with an upper bound of $6+1.5\times[(HR/60)-1]$ Hz and a lower bound of $0.9\times(HR/60)$ Hz, as described above. The system included 4 dual surface electrodes, where each dual electrode included one electrode for transmitting the radiofrequency output signals and one electrode for receiving the input signals. The signals were applied to and recorded from the left and right sides of the thorax; the signals were processed separately and averaged after digital processing.

The signal processing unit of the system determined the phase shift Ace) of the input radiofrequency signals relative to the output radiofrequency signals, applied the dynamically variable filter and calculated the cardiac output as further detailed hereinabove.

Nine subjects with Coronary Artery Disease (CAD) who underwent maximal exercise testing with simultaneous measurement of cardiac output using the direct Fick method are included for comparison purposes.

Statistical Analysis

Descriptive statistics are presented below as mean±standard deviation (SD). The associations between non-invasive cardiac output data, clinical variables and other exercise test responses were assessed using linear regression.

Results

Exercise Test Responses
Exercise test responses are summarized in Table 2.

TABLE 2

|  | CHF | Normal | p value |
|---|---|---|---|
| Rest |  |  |  |
| Standing heart rate (beats/min) | 73 ± 13 | 75 ± 13 | 0.72 |
| Systolic blood pressure (mmHg) | 121 ± 9 | 125 ± 9 | 0.23 |
| Ventilatory Threshold |  |  |  |
| Heart rate (beats/min) | 95 ± 28 | 136 ± 27 | <0.001 |
| Systolic blood pressure (mmHg) | 131 ± 12 | 139 ± 9 | 0.06 |
| Diastolic blood pressure (mmHg) | 80 ± 9 | 83 ± 8 | 0.48 |
| Oxygen uptake (ml/min) | 1046 ± 501 | 1517 ± 493 | 0.01 |
| Oxygen uptake (ml/kg/min) | 11.9 ± 4.4 | 20.9 ± 7.4 | <0.001 |
| Minute ventilation (l/min) | 32.0 ± 13.0 | 39.3 ± 13.8 | 0.14 |
| $CO_2$ production (ml/min) | 1005 ± 512 | 1492 ± 590 | 0.02 |
| Exercise time (min) | 7.4 ± 4.2 | 5.6 ± 3.1 | 0.23 |
| Perceived exertion | 4.5 ± 2.8 | — | — |
| Maximal Exercise |  |  |  |
| Heart rate (beats/min) | 103 ± 24 | 139 ± 24 | <0.001 |
| Systolic blood pressure (mmHg) | 134 ± 14 | 143 ± 12 | 0.04 |
| Oxygen uptake (ml/min) | 1310 ± 587 | 1857 ± 464 | 0.007 |
| Oxygen uptake (ml/kg/min) | 14.7 ± 5.4 | 24.8 ± 6.1 | <0.001 |
| Minute ventilation (l/min) | 49.4 ± 19.8 | 63.7 ± 16.5 | 0.03 |
| $CO_2$ production | 1442 ± 660 | 2173 ± 577 | 0.01 |
| Respiratory exchange ratio | 1.10 ± 0.08 | 1.15 ± 0.09 | 0.13 |
| Exercise time (min) | 10.7 ± 4.4 | 9.1 ± 2.1 | 0.21 |
| Perceived exertion | 7.8 ± 1.8 | — | — |

For the overall group, the mean maximal perceived exertion was 7.8±1.7 (range 5-10), and the mean peak respiratory exchange ratio was 1.12±0.09 (range 0.87-1.28), suggesting that maximal effort was achieved by most patients. Among CHF patients, the mean maximal heart rate of 103±24 beats/min (range 76-140) was lower than that expected for age (61% of predicted), reflecting the fact that many patients were limited by symptoms associated with CHF, that heart rate was limited by the effects of beta-blockade, or both. Mean maximal oxygen uptake for the CHF sample was 14.7±5.4 ml/kg/min (range 6.8-25.7) (representing 50.0±21% of age-predicted peak $VO_2$), and the ventilatory threshold occurred at 81% of peak $VO_2$. The wide ranges of each of these parameters indicate that the sample was diverse, which was desired for this initial evaluation.

Cardiac Output

Cardiac output measurements at rest and during exercise are presented in Table 3.

TABLE 3

|  | CHF | Normals | p value |
|---|---|---|---|
| Rest |  |  |  |
| Cardiac output (L/min) | 4.9 ± 1.5 | 5.7 ± 1.8 | 0.28 |
| Cardiac index (L/min/M²) | 2.5 ± 0.70 | 3.1 ± 0.7 | 0.06 |

TABLE 3-continued

|  | CHF | Normals | p value |
|---|---|---|---|
| Dx/dt (ohme/sec) | 122.0 ± 84.9 | 196.1 ± 108.5 | 0.13 |
| VET (msec) | 159.7 ± 21.2 | 172.5 ± 35.3 | 0.12 |
| Peak Exercise |  |  |  |
| Cardiac output (L/min) | 15.0 ± 6.6 | 20.1 ± 9.3 | 0.11 |
| Cardiac index (L/min) | 7.4 ± 3.0 | 11.0 ± 4.6 | 0.02 |
| Dx/dt (ohme/sec) | 377.2 ± 195.0 | 639.6 ± 188.2 | 0.01 |
| VET (msec) | 147.3 ± 21.2 | 141.3 ± 17.9 | 0.67 |

Among patients with CHF, cardiac output increased from 4.9±1.5 to 15.0±6.6 L/min at peak exercise, along with a concomitant increase in $d\Phi/dt_{max}$ (122.0±84.9 to 377.2±195.0 ohme/sec) and an 8% reduction in VET. Cardiac output among normal subjects was 16% and 34% higher than that of CHF patients at rest and during exercise, respectively.

Figure 8:
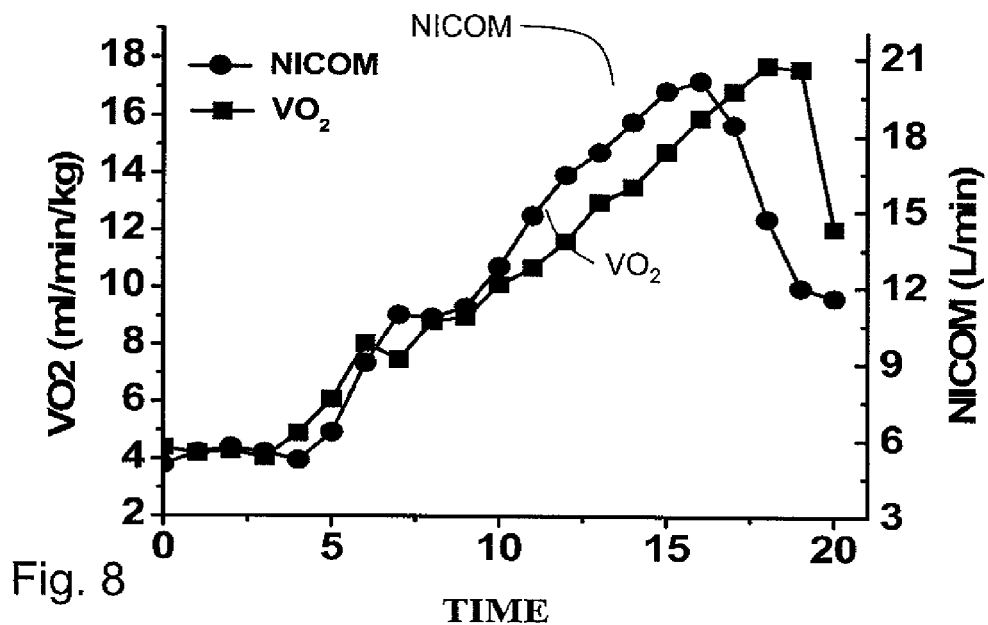
FIG. 8 is a graph showing mean values for oxygen uptake during exercise superimposed with mean changes in cardiac output in a typical patient with CHF as obtained according to some embodiments of the present invention.
Figure 9:
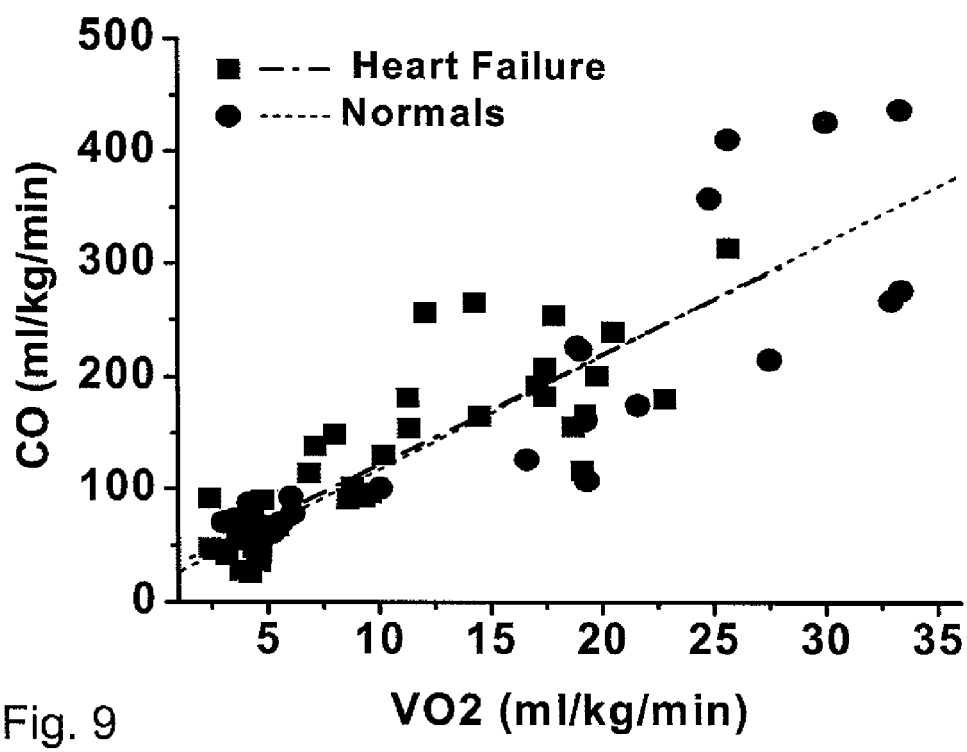
FIG. 9 is a graph showing the relationship between cardiac output and oxygen uptake at rest and peak exercise according to some embodiments of the present invention.

FIG. 8 illustrates the changes in oxygen uptake superimposed with estimated cardiac output over time in a typical example, demonstrating that they closely paralleled one another during the test. The relationship between cardiac output and oxygen uptake at rest and peak exercise is presented in FIG. 9. There is a strong association between cardiac output and oxygen uptake (r=0.89, p<0.001).

Figure 10:
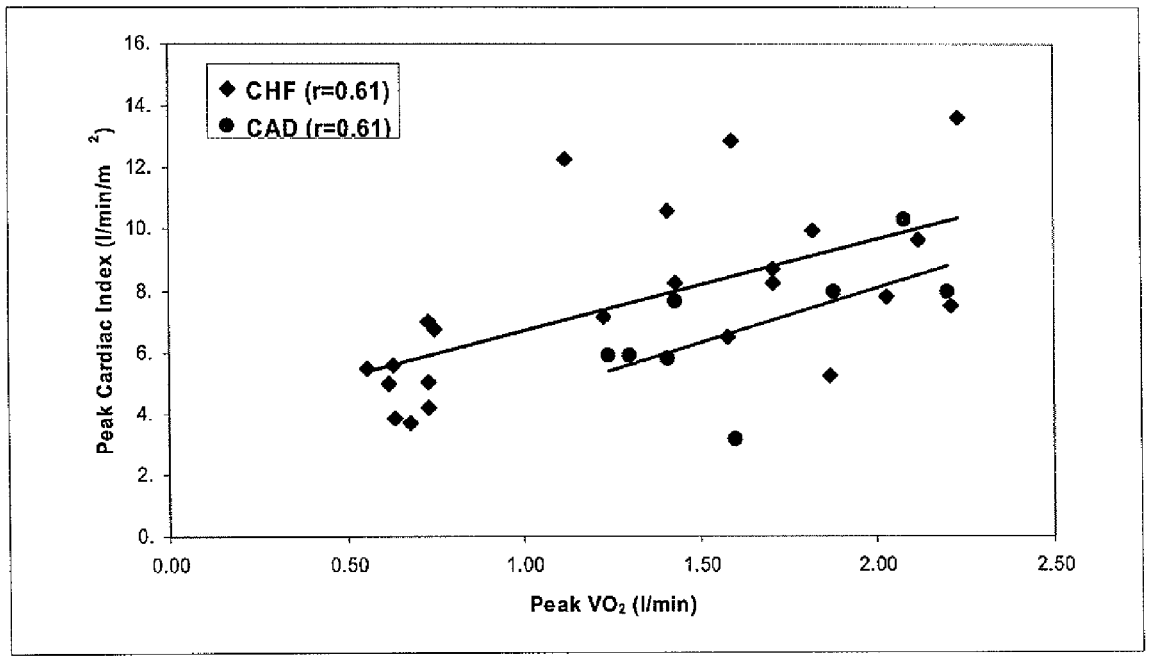
FIG. 10 is a graph showing relationships between peak cardiac index and peak $VO_2$ in CHF patients tested according to some embodiments of the present invention, and patients with CAD tested using a direct Fick method.

FIG. 10 shows relationships between peak cardiac index and peak $VO_2$ in CHF patients tested according to the present embodiments and patients with CAD tested using the direct Fick method. The relationships between peak cardiac index and peak $VO_2$ were similar for the directly measured (r=0.61) and non-invasive (r=0.61) methods.

Figure 11:
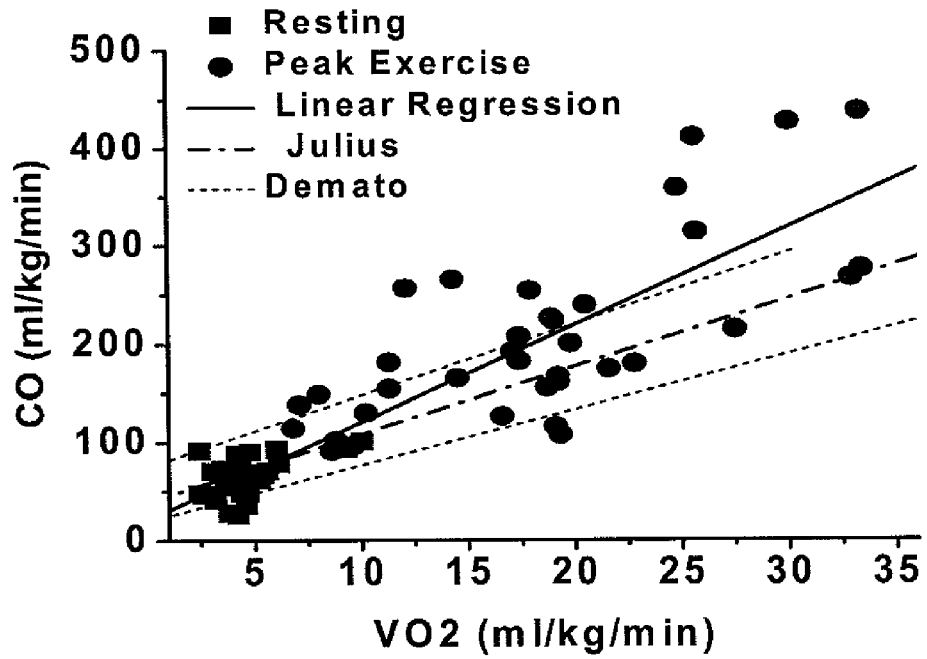
FIG. 11 is a graph showing the association between resting and peak exercise cardiac output and oxygen uptake according to some embodiments of the present invention, superimposed with other studies.

FIG. 11 presents the association between resting and peak exercise cardiac output and oxygen uptake obtained according to the present embodiments. The association is superimposed with other studies [Julius S, Amery A, Whitlock L S, Conway J. Influence of age on the hemodynamic response to exercise. *Circulation.* 1967; 36:222-230; and Damato A N, Galante J G, Smith W M. Hemodynamic response to treadmill exercise in normal subjects. *J. Appl Physiol* 1966; 21:959-966]. The relation between cardiac output and oxygen uptake was similar between the current study and the two earlier studies, as evidenced by the similar line of best fit (current and Julius study) and similar 95% confidence limits (current and Damato studies).

Table 3 below presents correlation coefficients between estimated cardiac output and key clinical and exercise test responses. In Table 3, values followed by an asterisk (*) refer to p<0.05, values followed by the pound sign (#) refer to p<0.01, CO refers to cardiac output in ml/kg/min, CI refers to cardiac index in L/min/m², dX/dt refers to the peak aortic flow, BP refers to blood pressure in mmHg, HR refers to heart rate, VET refers to ventricular ejection time in msec, refers to $VO_2VT$ refers to oxygen uptake at the ventilatory threshold in ml/kg/min, and OUES refers to oxygen uptake efficiency slope.

TABLE 3

|  | Rest CO | Rest CI | Rest dX/dt | Rest HR | Rest Syst. BP | Rest VET | Age | Eject. Frac. | Peak HR | Peak VO2 | VO2 VT | VE/ VCO2 | OUES | Max CO | Max CI | Max dX/dt |
|---|---|---|---|---|---|---|---|---|---|---|---|---|---|---|---|---|
| Rest CO | — |  |  |  |  |  |  |  |  |  |  |  |  |  |  |  |
| Rest CI | 0.96# | — |  |  |  |  |  |  |  |  |  |  |  |  |  |  |
| Rest dX/dt | 0.77# | 0.79# | — |  |  |  |  |  |  |  |  |  |  |  |  |  |

TABLE 3-continued

| | Rest CO | Rest CI | Rest dX/dt | Rest HR | Rest Syst. BP | Rest VET | Age | Eject. Frac. | Peak HR | Peak VO2 | VO$_2$ VT | VE/ VCO$_2$ | OUES | Max CO | Max CI | Max dX/dt |
|---|---|---|---|---|---|---|---|---|---|---|---|---|---|---|---|---|
| Rest HR | 0.54# | 0.57# | 0.37 | — | | | | | | | | | | | | |
| Rest Syst. BP | −0.27 | −0.22 | −0.23 | 0.00 | — | | | | | | | | | | | |
| Rest VET | 0.07 | −0.02 | −0.32 | −0.13 | 0.07 | — | | | | | | | | | | |
| Age | −0.27 | −0.28 | −0.16 | −0.07 | 0.01 | −0.15 | — | | | | | | | | | |
| Eject. Frac. | 0.04 | −0.04 | −0.10 | 0.17 | 0.28 | 0.38* | −0.24 | — | | | | | | | | |
| Peak HR | 0.48# | 0.48# | 0.20 | 0.36* | 0.09 | 0.37* | −0.49# | 0.35* | — | | | | | | | |
| Peak VO$_2$ | 0.36* | 0.28 | 0.18 | 0.21 | 0.05 | 0.34* | −0.52# | 0.41* | 0.67# | — | | | | | | |
| VO$_2$ VT | 0.24 | 0.15 | 0.07 | 0.04 | 0.09 | 0.36* | −0.58# | 0.42* | 0.56# | 0.91# | — | | | | | |
| VE/ VCO$_2$ | −0.04 | −0.08 | −0.09 | −0.09 | −0.37* | −0.03 | 0.56# | −0.09 | −0.41# | −0.59# | −0.61# | — | | | | |
| OUES | 0.19 | 0.26 | −0.16 | 0.13 | 0.11 | 0.20 | −0.48# | 0.15 | 0.55# | 0.81# | 0.76# | −0.66# | — | | | |
| Max CO | 0.18 | 0.17 | −0.05 | 0.10 | 0.13 | 0.34* | −0.58# | 0.19 | 0.60# | 0.73# | 0.74# | −0.47# | 0.67# | — | | |
| Max CI | 0.12 | 0.18 | −0.06 | 0.09 | 0.17 | 0.28 | −0.55# | 0.09 | 0.55# | 0.64# | 0.66# | −0.48# | 0.72# | 0.97# | — | |
| Max dX/dt | 0.48# | 0.49# | 0.30 | 0.19 | −0.02 | 0.08 | −0.61# | 0.00 | 0.46# | 0.55# | 0.63# | −0.39* | 0.50# | 0.79# | 0.78# | — |
| Max Syst. BP | −0.01 | 0.06 | −0.16 | 0.04 | 0.60# | 0.36* | −0.06 | 0.36* | 0.35* | 0.33* | 0.21 | −0.29 | 0.40* | 0.24 | 0.29 | 0.06 |

Both maximal cardiac output and cardiac index were strongly related to peak VO$_2$ (r=0.73 and 0.64, respectively, p<0.001). Peak VO$_2$ was modestly associated with resting cardiac output (r=0.36 and 0.28 for resting cardiac output and cardiac index, respectively), and resting estimates of parameters related to ventricular contractility (0.41 and 0.34 for EF and VET, respectively). Maximal d(I)/dt was strongly associated with both maximal cardiac output and cardiac index (r=0.79 and 0.78, respectively, p<0.001).

Figure 12:
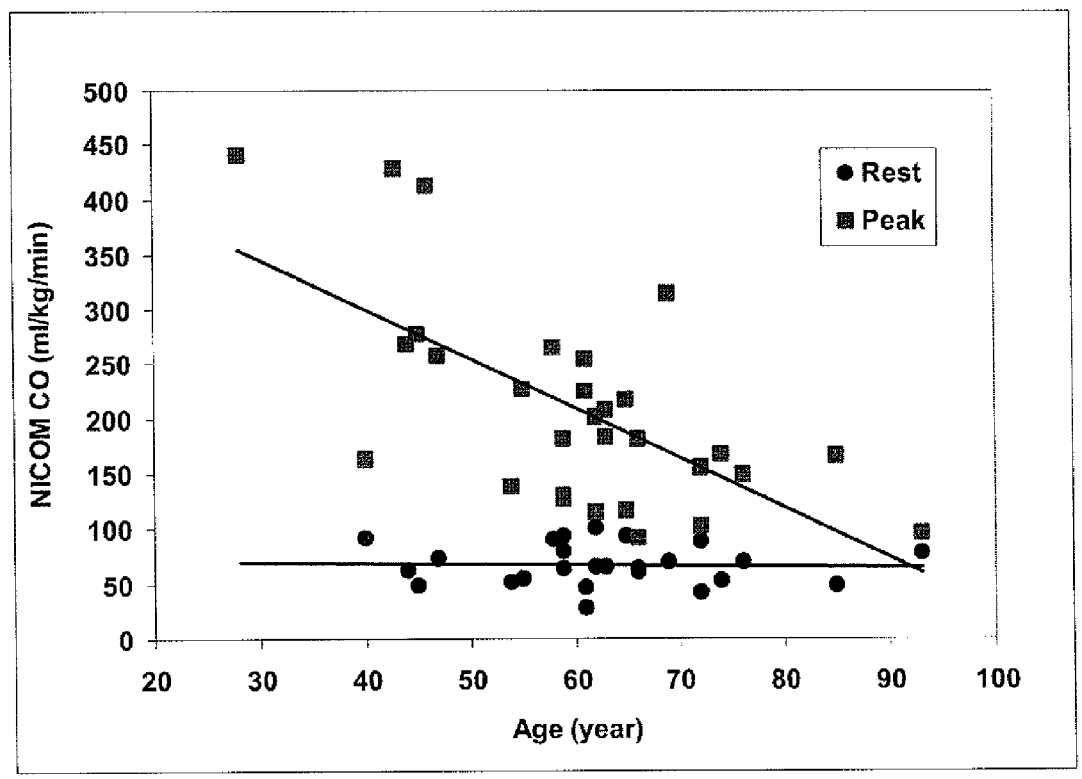
FIG. 12 is a graph showing the relationship between cardiac output as determined according to some embodiments of the present invention and age.

FIG. 12 shows the relationship between cardiac output as calculated according to some embodiments of the present invention and age. Shown in FIG. 12 are cardiac output values measured at rest (circles) and peak exercise (squares). Resting cardiac output was weakly associated with age (r=−0.27, ns), but a significant inverse association was observed at peak exercise (r=−0.58, p<0.001).

Figure 13:
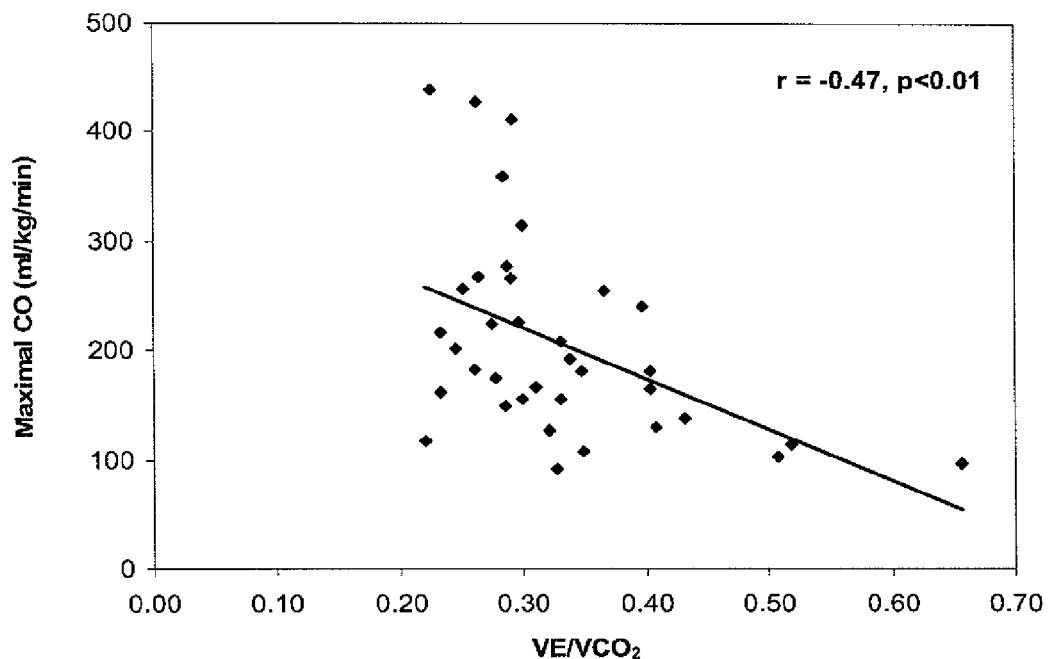
FIG. 13 is a graph showing the relationship between maximal cardiac output as calculated according to some embodiments of the present invention and the $VE/VCO_2$ slope.

FIG. 13 shows the relationship between maximal cardiac output as calculated according to some embodiments of the present invention and the VE/VCO$_2$ slope. Maximal cardiac output was inversely related to the VE/VCO$_2$ slope (r=−0.47, p<0.01). The VE/VCO$_2$ slope was also found to be have strong relation to VO$_2$ at peak exercise (r=−0.59, p<0.01) and VO$_2$ at the ventilatory threshold (r=−0.61, p<0.01).

Figure 14:
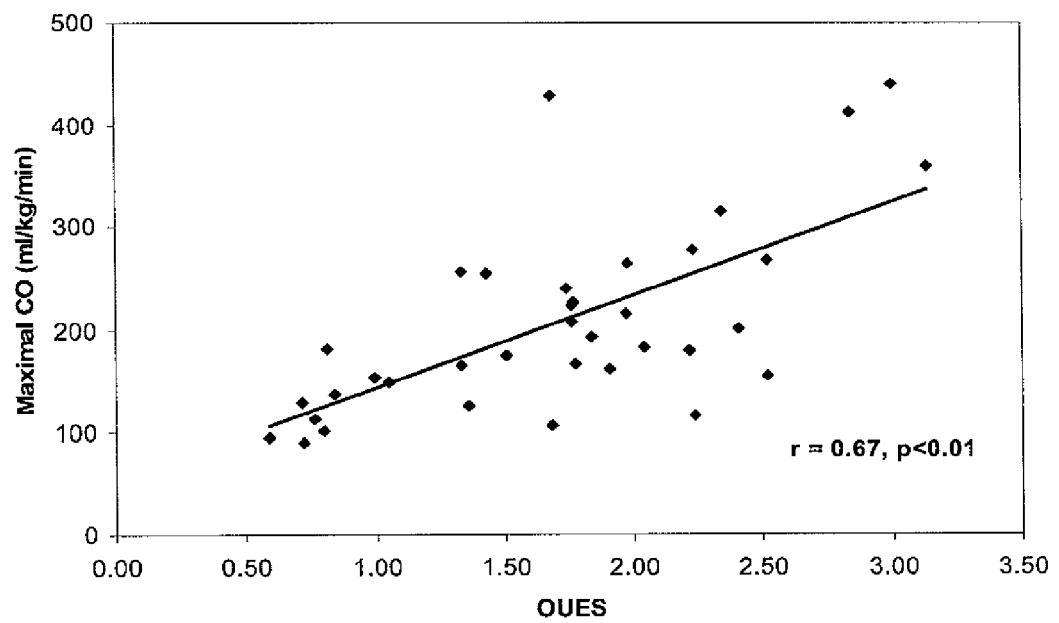
FIG. 14 is a graph showing the relationship between maximal cardiac output as calculated according to some embodiments of the present invention and the OUES.

FIG. 14 shows the relationship between maximal cardiac output as calculated according to some embodiments of the present invention and the OUES. Maximal cardiac output was directly related to the OUES (r=0.67, p<0.01). The OUES was also found to be have strong relation to VO$_2$ at peak exercise (r=0.81, p<0.001) and VO$_2$ at the ventilatory threshold (r=0.76, p<0.001).

DISCUSSION

The present example demonstrated the ability of some embodiments of the present invention to calculate cardiac output during exercise so as to estimate exercise capacity. A linear association between cardiac output as calculated according to some embodiments of the present invention and VO$_2$ at rest and during exercise has been demonstrated (r=0.89, p<0.001, FIG. 9). The calculated cardiac output and VO$_2$ closely paralleled one another throughout exercise (FIG. 18). Associations between peak VO$_2$ and peak calculated cardiac output (r=0.73) and peak cardiac index (r=0.64) were also observed. The relationships between peak cardiac index and peak VO$_2$ were similar for the directly measured (r=0.61) and non-invasive (r=0.61) methods (FIG. 10). Relatively modest associations were observed between resting cardiac output and exercise performance and direct association between the various estimates of cardiac performance and VO$_2$ at the ventilatory threshold were observed (Table 3).

The results presented in this example demonstrate that the present embodiments provide face validity for estimating exercise capacity, particularly, but not exclusively, in patients with CHF.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of estimating exercise capacity of a subject using output radiofrequency signals transmitted to the subject during exercise and input radiofrequency signals received from the subject during exercise, the method comprising:
using a data processor for:
determining a phase shift of the input radiofrequency signals relative to the output radiofrequency signals to provide processed signals;
filtering said processed signals using a dynamically variable filter characterized by a frequency band which is dynamically adapted in response to a change in a physiological condition of the subject;
calculating cardiac output based on said filtered and processed signal; and
using said cardiac output for estimating the exercise capacity of the subject.

2. The method of claim 1, further comprising obtaining at least one cardiopulmonary exercise testing (CPX) measure pertaining to a cardiopulmonary exercise testing, and combining said cardiac output with said at least one CPX measure to estimate the exercise capacity of the subject.

3. A method of estimating exercise capacity of a subject, comprising:
transmitting output radiofrequency signals to the subject during exercise;
receiving input radiofrequency signals from the subject during exercise; and
executing the method of claim 1.

4. The method of claim 1, further comprising reducing or eliminating amplitude modulation of said input radiofrequency signals so as to provide input radiofrequency signals of substantially constant envelope.

5. The method of claim 1, further comprising mixing said output radiofrequency signals and said input radiofrequency signals so as to provide a mixed radiofrequency signal, and filtering out a portion of said mixed radiofrequency signal so as to substantially increase a signal-to-noise ratio of a remaining portion of said mixed radiofrequency signal.

6. The method of claim 3, further comprising performing a cardiopulmonary exercise testing to provide at least one CPX measure and combining said cardiac output with said at least one CPX measure to estimate the exercise capacity of the subject.

7. Apparatus for estimating exercise capacity of a subject using output radiofrequency signals transmitted to the subject during exercise and input radiofrequency signals received from the subject during exercise, the apparatus comprising:
a phase shift determinator configured for determining a phase shift of the input radiofrequency signals relative to the output radiofrequency signals, to provide process signals;
a filtering unit configured for filtering said process signals using a dynamically variable filter characterized by a frequency band which is dynamically adapted in response to a change in a physiological condition of the subject;
a cardiac output calculator configured for calculating cardiac output based on said filtered and processed signal; and
an exercise capacity estimator configured for using said cardiac output for estimating the exercise capacity of the subject.

8. The apparatus of claim 7, wherein said exercise capacity estimator is configured for combining said cardiac output with at least one CPX measure to estimate the exercise capacity of the subject.

9. A system for estimating exercise capacity of a subject, comprising:
a radiofrequency generator for generating output radiofrequency signals;
a plurality of electrodes designed for transmitting said output radiofrequency signals to the subject and for sensing input radiofrequency signals from the subject; and
the apparatus of claim 7.

10. The system of claim 9, further comprising a cardiopulmonary exercise testing system configured to provide at least one CPX measure, wherein said exercise capacity estimator is configured for combining said cardiac output with at least one CPX measure to estimate the exercise capacity of the subject.

11. The apparatus of claim 7, wherein the apparatus further comprises an envelope elimination unit designed and configured for reducing or eliminating amplitude modulation of said input radiofrequency signals so as to provide input radiofrequency signals of substantially constant envelope.

12. The apparatus of claim 7, wherein the apparatus further comprises:
a mixer configured for mixing said output radiofrequency signals and said input radiofrequency signals, to provide a mixed radiofrequency signal; and
a radiofrequency filter for filtering out a portion of said mixed radiofrequency signal so as to substantially increase a signal-to-noise ratio of a remaining portion of said mixed radiofrequency signal.

13. The method of claim 1, wherein said cardiac output is calculated using a linear relationship between said phase shift and said cardiac output.

14. The method of claim 1, wherein said physiological condition is a heart rate of the subject.

15. The method of claim 14, wherein a lower frequency bound characterizing said filter is about $0.9*(HR/60)$ Hz at all times, wherein said HR is said heart rate in units of beats per minute.

16. The method of claim 14, wherein an upper frequency bound characterizing said filter is about $6+1.5*[(HR/60)-1]$ Hz at all times, wherein said HR is said heart rate in units of beats per minute.

17. The method of claim 2, wherein said at least one CPX measure comprises ratio of ventilation efficiency to carbon dioxide production rate.

18. The method of claim 2, wherein said at least one CPX measure comprises oxygen uptake efficiency slope.

19. The Apparatus of claim 7, wherein said physiological condition is a heart rate of the subject.

20. The Apparatus of claim 19, wherein a lower frequency bound characterizing said filter is about $0.9*(HR/60)$ Hz at all times, wherein said HR is a heart rate in units of beats per minute.

21. The Apparatus of claim 19, wherein an upper frequency bound characterizing said filter is about $6+1.5*[(HR/60)-1]$ Hz at all times, wherein said HR is said heart rate in units of beats per minute.

* * * * *